US012618080B2

(12) United States Patent
Atarashi et al.

(10) Patent No.: US 12,618,080 B2
(45) Date of Patent: *May 5, 2026

(54) SOLANACEOUS PLANT AND SOLANACEOUS PLANT CELL HAVING RESISTANCE TO TOMATO SPOTTED WILT VIRUS, AND METHOD FOR PRODUCING SOLANACEOUS PLANT

(71) Applicants: KIKKOMAN CORPORATION, Noda (JP); NATIONAL UNIVERSITY CORPORATION HOKKAIDO UNIVERSITY, Sapporo (JP)

(72) Inventors: Hiroki Atarashi, Chiba (JP); Kenji Nakahara, Hokkaido (JP)

(73) Assignees: KIKKOMAN CORPORATION, Noda (JP); NATIONAL UNIVERSITY CORPORATION HOKKAIDO UNIVERSITY, Sapporo (JP)

( * ) Notice: Subject to any disclaimer, the term of this patent is extended or adjusted under 35 U.S.C. 154(b) by 862 days.

This patent is subject to a terminal disclaimer.

(21) Appl. No.: 17/788,160

(22) PCT Filed: Dec. 7, 2020

(86) PCT No.: PCT/JP2020/045381

§ 371 (c)(1),
(2) Date: Jun. 22, 2022

(87) PCT Pub. No.: WO2021/131628

PCT Pub. Date: Jul. 1, 2021

(65) Prior Publication Data

US 2023/0030612 A1 Feb. 2, 2023

(30) Foreign Application Priority Data

Dec. 24, 2019 (JP) ................................ 2019-232766

(51) Int. Cl.
*C12N 15/82* (2006.01)

(52) U.S. Cl.
CPC ................................ *C12N 15/8283* (2013.01)

(58) Field of Classification Search
CPC ............................ C12N 15/8283; A01H 6/00
See application file for complete search history.

(56) References Cited

FOREIGN PATENT DOCUMENTS

| | | | | |
|----|------------------|----------|----------|------------|
| EP | H0558944 A2 | 2/1993 | | |
| EP | 3888452 A1 | 10/2021 | | |
| JP | H0690758 A | 4/1994 | | |
| JP | H06343469 A | 12/1994 | | |
| WO | 2013010064 A | 1/2013 | | |
| WO | WO-2013010064 A1 * | 1/2013 | ......... | C12N 15/8218 |
| WO | 2015090468 A1 | 6/2015 | | |

OTHER PUBLICATIONS

Koonin et al., 2003, Evolutionary Concept in Genetics and Genomics. In: Sequence—Evolution—Function. Springer, Boston, MA. https://doi.org/10.1007/978-1-4757-3783-7_3, pp. 1-16. (Year: 2003).*
Bowen et al. (Published: 2002, Genomes. 2nd edition. Oxford: Wiley-Liss, Chapter 7 Understanding a Genome Sequence, pp. 1-32). (Year: 2002).*
Andolfo et al. (Published: 2013, Journal: New Phytologist 197: 223-237). (Year: 2013).*
Habbak et al. (Published: 2013, Dissertation submitted to College of Agriculture at the University of Kentucky). (Year: 2013).*
Huang et al. (Published Year: 2024, Journal: Frontiers in Plant Science, 10.3389/fpls.2024. 1503773, pp. 1-14). (Year: 2024).*
Guo et al. (Published Year: 2004, Journal: Proceedings of the National Academy of Sciences, vol. 101(25), pp. 9205-9210) . (Year: 2004).*
Jacobs et al. (Published Year: 2017, Journal: Plant Physiol. vol. 174, pp. 2023-2037). (Year: 2017).*
Qi et al. (Published Year: 2025, Journal: Horticulture Research, uhaf019, https://doi.org/10.1093/hr/uhaf019). (Year: 2025).*
Padmanabhan et al. (Published: May 21, 2019) Journal: Scientific Reports, 9:7673 | https://doi.org/10.1038/s41598-019-44100-x). (Year: 2019).*
Ejima et al. (NCBI GenBank, locus BAK52388 from S. lycopersicum, accession AB645823.1, Published: Jul. 13, 2011). (Year: 2011).*
Jacobs et al. (Published Year: 2017, Journal: Plant Physiol. vol. 174, pp. 2023-2037) Supplementary Data. (Year: 2017).*
Ejima et al. (NCBI GenBank. AB645834.1, Jun. 13, 2011, Accessed Mar. 5, 2025 from https://www.ncbi.nlm.nih.gov/.) (Year: 2011).*
Ejima et al. (NCBI GenBank. BAK52388, Jul. 13, 2011, Accessed Mar. 4, 2025 from https://www.ncbi.nlm.nih.gov/.) (Year: 2011).*
Simbaqueba et al., 2012, GenEmbl Database, LOCUS JO140982, mRNA, linear TSA Aug. 14, 2012, Physalis peruviana Php00a06957. 16910 mRNA sequence (Database result included in the office action). (Year: 2012).*

(Continued)

*Primary Examiner* — David H Kruse
*Assistant Examiner* — Santosh Sharma
(74) *Attorney, Agent, or Firm* — CANTOR COLBURN LLP

(57) ABSTRACT

The present invention addresses the problem of providing: a solanaceous plant and a solanaceous plant cell that have resistance to tomato spotted wilt virus (TSWV) and that have the property of inhibiting TSWV infection, the property of suppressing the propagation of TSWV after infection, and/or the property of suppressing the onset of the symptoms of TSWV infection; and a method for producing the solanaceous plant. The present invention provides a solanaceous plant that has resistance to TSWV, in which at least one gene selected from the group consisting of receptor-like kinase RLK genes and homologous genes thereof has a mutation, and in which as a result of the mutation, either the expression of the gene having the mutation is suppressed or a protein encoded by the gene having the mutation is non-functional with respect to TSWV.

8 Claims, 5 Drawing Sheets

Specification includes a Sequence Listing.

(56) References Cited

OTHER PUBLICATIONS

JPO Extended European Search Report for corresponding EP Application No. 20907296.6; Issued Jan. 3, 2024; 9 pages.

Zhu, et al. "Paving the Way to Tospovirus Infection: Multilined Interplays with Plant Innate Immunity"; Annual Reviews; Annual Review of Phytopathology; 2019, vol. 57, pp. 41-62.

Abel et al., "Delay of Disease Development in Transgenic Plants That Express the Tobacco Mosaic Virus Coat Protein Gene"; American Association for the Advancement of Science, May 9, 1986, New Series vol. 232, No. 4751: pp. 738-743.

Adkins, "Tomato spotted wilt virus-positive steps towards negative success"; Molecular Plant Pathology, (2000), 1(3): pp. 151-157.

Brommonschenkel et al. "Map-based cloning of the tomato genomic region that spans the SW-5 tospovirus resistance gene in tomato"; Mol. Gen. Genet., (1997), 256: pp. 121-126.

Gonsalves, "Control of Papaya Ringspot Virus in Papaya: A Case Study"; Annual Review Phytopathology, (1998), 36: pp. 415-437.

International Search Report for International Application No. PCT/JP2020/045381; Date of Mailing, Jan. 26, 2021.

Lopez et al., "Evolutionary analysis of tomato Sw-5 resistancebreaking isolates of Tomato spotted wilt virus"; Journal of General Virology; (2011), 92: pp. 210-215.

Okuda, "Tospoviruses occurring in and outside Japan"; Jpn. J. Phytopathol. 82 (2016): pp. 169-184; with English abstract only.

Scholthof et al., "Top 10 plant viruses in molecular plant pathology"; Molecular Plant Pathology; (2011), 12(9): pp. 938-954.

Tsuda, "Uirusu (Virus)-Tomato Spotted silt tospovirus: Plant-infecting bunyaviridae"; Plant Biotechnology Institute; (1999), 49(2): pp. 119-130.

* cited by examiner

SEQ ID NO:1

```
GTTACAAAAAAGAGTTGGGGCCTCCTCTACTTGTACAATCTCACAATTCAAATTTTATTTCTTTATAATAATCAATCCCTTC
GTATTATATTTATTTACTGAAAACAAAAGAATATACACACCAAACGGATTACCGACCGTCAAACCAAATGCTCATTTTTGGC
TTTCTCACTCTAACTGAGTGAAACTGCAAACCAAACAGTAGGTGGGCGTTAGATTAACGAAGCAAAAATGCGTCTTCTTTTT
TTTCTTCTTCTTCTTATGCATTTTACTGACTTTTCTGCCGGTAAACAACCACGCTTACCGGAATACCAGGCTTTGCTTGCCC
TGAAAACTGCCATTACCGATGACCCGCAGTTAACTCTTGCCTCATGGAACATCTCCACCAGTCACTGTACGTGGAATGGTGT
CACGTGCGACACGCATCGTCACGTGACCTCTCTTGATATTTCTGGGTTTAATCTTACCGGTACTCTTCCGCCGGAAGTTGGA
AATCTTCGTTCTTACAAAATTTGTCTGTTGCTGTTAACCAGTTTACTGGACCTGTACCTGTTGAAATCTCCTTTATTCCAA
ATCTGAGTTACCTTAATCTTTCTAATAACATATTCGGGATGGAATTCCCTTGGCAGTTAACACGTCTGCGTAACCTCCAAGT
CCTTGACCGTTTACAACAACAATATGACCGGTGAACTTCCCGTTGAGGTGTATCAGATGACTAAAGTTCGACATCTACACCTA
GGCGGGAACTTTTTCAGTGGCCGCATTCCTCCGGAGTATGGAAGATTCCCGTCTCTAGAGTACCTTGCAGTTTCAGGCAATG
GATTGGTAGGAGAGATACCACCGGAGATTGGAAACATCGCTACACTTCAGCAGTTGTATGTAGGATACTACAATACCTTCAC
CGGTGGGATTCCACCGGCAATAGGGAACTTATCGCAGCTCCTTCGGTTTGATGCTGCTAACTGTGGACTTTCGGGGAAGATT
CCACCGGAGATTGGGAAGCTTCAGAACCTTGATACCCTCTTCCTGCAAGTGAATTCTCTATCTGGATCTTTAACTCCGGAGA
TAGGTTATCTGAAGAGCTTGAAATCTTTGGATCTGTCGAATAACATGTTCTCTGGCGAGATACCGCCGACATTTGCGGAGCT
TAAGAATATCAGTCTTGTTAATCTTTTCCGGAATAAGCTTTATGGGTCAATACCAGAGTTCATAGAGGACTTGCCGGAACTA
GAGGTGTTGCAACTTTGGGAAAATAACTTTACTGGAAGCATTCCTCAGGGGTTAGGCACAAAGAGCAAGCTCAAAACTCTTG
ATCTCAGTTCCAATAAATTAACGGGAAATTTACCCCCAAACATGTGCTCCGGTAACAATCTGCAGACAATTATCACTCTAGG
GAACTTCTTGTTTGGGCCCAATTCCTGAATCTTTGGGTAGGTGTGAATCACTTAATGGTATTAGAATGGGAGAAAATTATCTG
AATGGGTCTATTCCAAAAGGGCTCTTAAGCTTGCCACATCTGTCACAAGTTGAACTTCAGAATAATATTCTCACTGGTACAT
TTCCTGATATTTCTTCCAAATCTAACAGTCTTGGCCAGATTATCCTTTCAAATAATCGCTTAACTGGACGTTTGCCACCAAG
GATTGGAAACTTTGCTGTAGCCCAAAAATTGCTTCTTGATGGGAACAAATTTTCGGGACGAATTCCAGCTGAAATAGGAAAG
CTTCAACAGCTATCCAAAATTGATTTCAGTCATAACAACTGTCTGGACCCATTGCTCCGGAGATTAGCCAGTGCAAGTTGC
TGACTTATGTTGATCTCAGCAGGAACCAACTTTCGGGTGAGATTCCTACTGAGATCACAGGTATGAGAATACTCAACTACTT
GAATTTATCGCGAAACCACTTAGTTGGGAGTATTCCTGCCCCTATTTCTAGTATGCAGAGTTTAACTTCTGTTGATTTGTCG
TATAACAACTTTTCTGGTTTAGTTCCTGGAACCGGGCAATTTAGTTATTTCAATTACACCTCATTTCTAGGCAATCCAGATC
TTTGCGGACCCTATTTGGGCCCTTGCAAAGAGGGCGTTGTTGATGGGGTTAGTCAACCTCACCAACGAGGAGCCTTAACGGCC
TTCGATGAAGCTTTTACTTGTTATAGGTTTGCTTGTCTGTTCTATTGTGTTTGCTGTTGCTGCAATTATAAAGGCCCGATCT
TTAAAGAAGGCAAGTGAAGCTCGTGCCTGGAAGCTAACTGCTTTTCAGCGGCCTGGATTTTACTTGTGATGATATTTGGATA
GCTTGAAGGAGGATAACGTTATTGGAAAAGGAGGTGCTGGTATTGTCTACAAGGGGGTAATGCCTAGCGGGGAACATGTAGC
GGTTAAGAGGTTGCCAGCTATGAGCAGGGGTTCCTCTCATGATCATGGGTTCAATGCAGAGATACAGACTCTTGGGAGGATC
CGACACAGGCACATTGTTAGATTATTAGGGTTTTGCTCGAATCATGAGACAAATCTTTGGTTTACGGAGTACATGCCTAATG
GAAGTCTTGGGGAAATGCTTCATGGCAAGAAAGGCGGTCATTTACATTGGGATACCAGGTATAAGATTGCCTTGGAGTCTGC
TAAGGGTCTTTGCTATCTCCATCACGATTGCTCTCCTTTGATCCTCCATCGGTGATGTGAAATCAAACAACATTCTGCTGGAC
TCCAGCTTTGAAGCTCATGTTGCTGATTTTGGACTTGCTAAGTTCTTGCAAGATTCAGGGACATCAGAATGCATGTCTGCTA
TTGCTGGTTCTTATGGGTACATTGGCTCCAGAATATGCTTACACACTTAAGGTTGATGAGAAGAGTGATGTATATAGCTTCGG
TGTGGTGCTACTAGAACTGGTAAGTGGCAAAAAACCAGTTGGAGAATTTGGTGATGGTGTTGACATAGTCCAATGGGTTAGG
AAAATGACTGATGGGAAAAAGGATGGAGTTCTCAAGATCCTTGACCCAAGACTCTCAACGGTTCCCCTTAATGAGGTGATGC
ATGTCTTCTATGTCGGCATTGTTGTGTGTCGGAAGAGCAGGCTGTGGAACGTCCCACCATGCGAGAGGTAGTGCAAATACTAAC
GGAACTTCCCAAGCCACCAGGTGCAAAATCAGATGACTCAACCGTCACTGATCAGTCGCCCCCATCAGCCTCTGCATTAGAG
TCCCGAACCTCAATTGCCGGGGACACAAAGACCATCATGAACGAACACCTCAATCACCTCCACCTGACCTACTCAGTATCT
AATTTGCAATGTTCTTGAAGTAGGAGTGTTTTATTTAGTTTGATTCTCTAGTTCTATTATGATCAATTGTGCTAAGCTTTAT
TCCTTTGTTTTAAAAAAATTGGGTCTTTCTAGGCTCGGGGGGTTTATTCTAACTCTAAGATGGGTTTAATGCTCAGAAGTTTT
CCTCTTGTACAGTAAGATTGGTAGGGTTTTCAAGTGTATTATTAAAATGGAAAAAAATTGCCCTTCATTTGCT
```

FIG. 1

```
Wild-type:    TCTCTAGAGTACCTTGCAGT                         (SEQ ID NO: 3)

Mutant R-A:   TCT------GTACCTTGCAGT    (5 nt deletion)     (SEQ ID NO: 8)

Mutant R-B:   TCTACTAGAGTACCTTGCAGT    (1 nt insertion)    (SEQ ID NO: 9)
```

FIG. 6

SOLANACEOUS PLANT AND SOLANACEOUS PLANT CELL HAVING RESISTANCE TO TOMATO SPOTTED WILT VIRUS, AND METHOD FOR PRODUCING SOLANACEOUS PLANT

CROSS REFERENCE TO RELATED APPLICATIONS

This is the U.S. national stage of application No. PCT/JP2020/045381, filed on Dec. 7, 2022. Priority under 35 U.S.C. § 119(a) and 35 U.S.C. § 365(b) is claimed from Japanese Application No. 2019-232766 filed Dec. 24, 2019, the disclosure of which is also incorporated herein by reference.

TECHNICAL FIELD

The present invention relates to a solanaceous plant resistant to tomato spotted wilt virus, a solanaceous plant cell, and a method for producing the solanaceous plant.

BACKGROUND ART

In accordance with the increase in commercial distribution of agricultural products, viral diseases, which have been localized in the past, begun to spread throughout the world. Representatives of such viruses are viruses of genus *Tospovirus* belonging to the family Bunyaviridae and of genus *Begomovirus* belonging to the family Geminiviridae.

Tomato spotted wilt virus (hereinafter, frequently abbreviated to "TSWV") is a very important virus causing scientific and economic impact and is ranked in top five among various plant viruses.

Tomato spotted wilt virus is first discovered in 1915 and is one of the viruses having relatively long history. However, study of this virus have been delayed due to difficulty in purifying a complete virion. Number of studies began to finally increase in 1990's, and now, the virus is classified as a type virus of the genus *Orthotospovirus* of the family Tospoviridae (see, for example, NPL 1). In the family Bunyaviridae, there are four other genera in addition to the genus *Tospovirus*, and the viruses of these other genera infect animals. Therefore, this family is taxonomically very special virus group which include animal viruses and plant viruses in the same family (see, for example, NPL 2 and NPL 3).

TSWV is a spherical virus having an envelope with a diameter of about 100 nm, and having a trisegmented, closed circular filament-shaped nucleocapsid therein. The viral genome is single-stranded RNA which is also triple-segmented, and goes through genetic translation basically as a minus strand.

A large factor causing worldwide outbreaks of viruses of the genus *Tospovirus*, such as TSWV, and of the genus *Begomovirus* of the family Geminiviridae, such as tomato yellow leaf curl virus (TYLCV), is the extension of the distribution of insect vectors in accordance with the globalization of the commercial distribution. The important insect vectors for both viruses have expanded their distribution by attaching to agricultural products including flowers.

TSWV is mainly transmitted by *Thysanoptera*, very small insects of about 1 mm in body length. Various species of *Thysanoptera*, such as soybean thrips, onion thrips, western flower thrips, and flower thrips, are known to mediate the virus. Thrips is capable of acquiring TSWV only in larval stage by sap-sucking, and although larva before eclosion also has infectivity, the TSWV infection generally occurs through sap-sucking by adult insects. At the beginning, thrips mediating TSWV were native species, such as flower thrips and thrips setosus, but western flower thrips, known as an important vector for TSWV, entered Japan in 1990 from overseas. In accordance with the expansion of western flower thrips by its ability to move long distances, occurrence of TSWV changed drastically.

As *Thysanoptera* prefers pollen, viruses of genus *Tospovirus*, including TSWV, cause drastic damages to various flowers and also to vegetables cultivated next to flower fields. Host spectrum of TSWV is very broad, including 900 or more plants, and nowadays, worldwide occurrence of TSWV is seen mainly in vegetables and flowering plants, including tomato, bell pepper, tobacco, melon, chrysanthemum, dahlia, and eustoma (see, for example, NPL 4). Further, TSWV is able to infect weeds of *Asteraceae, Polygonaceae*, and the like, and some plants overwinter and become infection source next year. Once the virus of the genus *Tospovirus* infect a plant, they are likely to be localized and masked in plants, thus, these viruses are difficult to remove.

So far, the measures for preventing the TSWV disease are either by breeding resistant varieties, complete extermination of thrips, or early removal of plants infected with TSWV. Thrips is a very small insect with a length of 1 mm or less, and the greenhouse must be covered with fine-mesh net to control the invasion of thrips. However fine-mesh net may cause increasing temperature in the greenhouses, this control is actually hesitated. In addition, as thrips prefers pollen and dives into perianth, pesticides is not effective.

As a plant breeding conferring TSWV resistance, for example, in 1998, resistant gene Sw-5 was isolated from wild-relatives tomato *Solanum peruvianum* L. having resistance to TSWV, and was introgressed into general cultivars (see, for example, NPL 5). Sw-5 was a promising resistant gene in tomato, however resistance-overcoming strains of TSWV emerged in different places worldwide before becoming popular use of this resistance gene (see, for example, NPL 6). Similar phenomenon occurred for the TSWV-resistant gene Tsw in the genus *Capsicum*. Such phenomena are frequently seen in dominant resistant genes, and at the present, there is only a scarce source of effective resistant genes.

Other genetic engineering methods include a method for providing virus resistance to plants by the so-called genetic recombination where a viral coat protein gene of TSWV or a gene sequence complementary to at least a part of an RNA replicative intermediate of the virus is introduced into a plant genome by genetic engineering and plant transformation. Such a method has been developed for tobacco, tomato, potato and papaya (see, for example, NPL7 and 8, and PTL 1 and 2).

Commercial cultivation of the above-mentioned genetically engineered plants are still difficult in many countries over the world. Even in countries capable of cultivating the genetically modified plants, at the present, many experimental verifications are required.

CITATION LIST

Patent Literature

PTL 1
Japanese Patent Application Laid-Open No. Hei 6-90758
PTL 2
Japanese Patent Application Laid-Open No. Hei 6-343469

US 12,618,080 B2

3

Non-Patent Literature

NPL 1
SCHOLTHOF et al., "MOLECULAR PLANT PATHOL-
OGY," 2011, 12(9): 938-954
NPL 2
Tsuda, "Uirusu (Virus)," 1999, 49(2):119-130
NPL 3
Adkins, "MOLECULAR PLANT PATHOLOGY," 2000,
1(3): 151-157
NPL 4
Okuda, "Journal of Phytopathological Society of Japan,"
2016, 82:169-184
NPL 5
Brommonschenkel et al., "Mol Gen Genet," 1997, 256:
121-126
NPL 6
Lo' pez et al., "Journal of General Virology," 2011, 92:
210-215
NPL 7
Abel et al., "Science," 1986 May 9; 232(4751):738-743
NPL 8
Gonsalves, "Annu. Rev. Phytopathol.," 1998, 36:415-437

SUMMARY OF INVENTION

Technical Problem

As explained above, preventive methods for the plant disease by TWSV include the following methods:

(1) Control of thrips which transmit TSWV;

(2) Development of a TSWV resistant variety;

(3) Development of a TSWV resistant transgenic plant by genetic recombination; and (4) Development of attenuated virus for controlling TSWV.

Methods (1) and (3) are difficult for the above-mentioned reasons. Practice of method (4) is difficult unless there is no or very small side effects of the attenuated virus on plant growth. Up to today, no effective attenuated virus of TSWV has been developed for solanaceous plants.

Under the above-mentioned circumstances, the present inventors have conducted an intensive research for a method for preventing the plant disease by TSWV using the above method (2). As a result, the present inventors found a novel resistant gene. The task of the present invention is to provide a method for preventing TSWV and a TSWV resistant plant by developing a plant variety harboring this gene.

Solution to Problem

The present invention relates to the following solanaceous plant, parts of the plant, and processed material thereof.

[1] A solanaceous plant having a mutation in at least one gene selected from a group consisting of receptor-like kinase RLK gene and a gene homologous thereto, wherein the mutation either inhibits expression of the mutated gene or makes a protein encoded by the mutated gene to be non-functional for tomato spotted wilt virus, and wherein the solanaceous plant has virus resistance against the tomato spotted wilt virus.

[2] The solanaceous plant according to [1], wherein the mutation is a genomic gene mutation introduced by genome editing techniques.

[3] The solanaceous plant according to [1] or [2], wherein the mutation is at least one type of mutation selected from (a) to (d) below:

(a) a frameshift mutation, (b) a nonsense mutation, (c) a loss of continuous or non-continuous 3n nucleotides (wherein n=1 to 7), and (d) a replacement, deletion, addition, and/or insertion of 1 or more nucleotides.

[4] The solanaceous plant according to any one of [1] to [3], wherein the mutation is in the receptor-like kinase RLK gene or the gene homologous thereto.

[5] The solanaceous plant according to [4], wherein the receptor-like kinase RLK gene has a cDNA sequence comprising a nucleotide sequence as set forth in SEQ ID NO:1, and the gene homologous to the receptor-like kinase RLK gene has a cDNA sequence comprising a nucleotide sequence which has at least 85% homology to the nucleotide sequence as set forth in SEQ ID NO:1.

[6] The solanaceous plant according to [5], wherein the receptor-like kinase RLK gene or the gene homologous thereto has the mutation in a region corresponding to a nucleotide sequence as set forth in SEQ ID NO:3.

[7] The solanaceous plant according to [6], wherein the region corresponding to the nucleotide sequence as set forth in SEQ ID NO:3 is mutated to a nucleotide sequence as set forth in SEQ ID NO:8 or 9.

[8] The solanaceous plant according to any one of [1] to [7] which is tomato.

[9] A part of the solanaceous plant according to any one of [1] to [8].

[10] The part of the solanaceous plant according to [9] which is a fruit.

[11] The part of the solanaceous plant according to [9] which is a seed.

[12] A processed material of the solanaceous plant or the part thereof according to any one of [1] to [11].

[13] The processed material according to [12] which is edible.

Further, the present invention relates to the following solanaceous plant cell, and a plant and a part thereof comprising the cell.

[14] A solanaceous plant cell having a mutation in at least one gene selected from a group consisting of receptor-like kinase RLK gene and a gene homologous thereto, wherein the mutation either inhibits expression of the mutated gene or makes a protein encoded by the mutated gene to be non-functional for tomato spotted wilt virus, and wherein the solanaceous plant has virus resistance against the tomato spotted wilt virus.

[15] The solanaceous plant cell according to [14], wherein the mutation is a genomic gene mutation introduced by genome editing techniques.

[16] The solanaceous plant cell according to [14] or [15], wherein the mutation is at least one type of mutation selected from (a) to (d) below:

(a) a frameshift mutation, (b) a nonsense mutation, (c) a loss of continuous or non-continuous 3n nucleotides (wherein n=1 to 7), and (d) a replacement, deletion, addition, and/or insertion of 1 or more nucleotides.

[17] The solanaceous plant cell according to any one of [14] to [16], wherein the mutation is in the receptor-like kinase RLK gene or the gene homologous thereto.

[18] The solanaceous plant cell according to [17], wherein the receptor-like kinase RLK gene has a cDNA sequence comprising a nucleotide sequence as set forth in SEQ ID NO:1, and the gene homologous to the receptor-like kinase RLK gene has a cDNA sequence comprising a nucleotide sequence which has at least 85% homology to the nucleotide sequence as set forth in SEQ ID NO:1.

[19] The solanaceous plant cell according to [18], wherein the receptor-like kinase RLK gene or the gene homologous thereto has the mutation in a region corresponding to a nucleotide sequence as set forth in SEQ ID NO:3.

[20] The solanaceous plant cell according to [19], wherein the region corresponding to the nucleotide sequence as set forth in SEQ ID NO:3 is mutated to a nucleotide sequence as set forth in SEQ ID NO:8 or 9.

[21] The solanaceous plant cell according to any one of [14] to [20], wherein the solanaceous plant is tomato.

[22] A solanaceous plant and a part thereof comprising the solanaceous plant cell according to any one of [14] to [21], and having virus resistance against tomato spotted wilt virus.

[23] The part of the solanaceous plant according to [22] which is a fruit.

[24] The part of the solanaceous plant according to [22] which is a seed.

[25] A processed material of the solanaceous plant or the part thereof according to any one of [22] to [24].

[26] The processed material according to [25] which is edible.

Further the present invention provides the following method for producing a solanaceous plant and a solanaceous plant produced by the method.

[27] A method for producing a virus resistant solanaceous plant which is resistant to tomato spotted wilt virus, the method comprising: selecting at least one gene from a group consisting of receptor-like kinase RLK gene and a gene homologous thereto; introducing a mutation into the selected gene in a genome, wherein the introduced mutation is either a mutation inhibiting an expression of the mutated gene or a mutation making a protein encoded by the mutated gene to be non-functional for the tomato spotted wilt virus; and selecting a solanaceous plant having resistance to the tomato spotted wilt virus.

[28] The method for producing a virus resistant solanaceous plant according to [27], wherein the mutation is introduced into the gene in the genome by genome editing techniques.

[29] The method for producing a virus resistant solanaceous plant according to [27] or [28], wherein the mutation is at least one type of mutation selected from (a) to (d) below:

(a) a frameshift mutation,
(b) a nonsense mutation,
(c) a loss of continuous or non-continuous 3n nucleotides (wherein n=1 to 7), and
(d) a replacement, deletion, addition, and/or insertion of 1 or more nucleotides.

[30] The method for producing a virus resistant solanaceous plant according to any one of [27] to [29], wherein the mutation is introduced into the receptor-like kinase RLK gene or the gene homologous thereto.

[31] The method for producing a virus resistant solanaceous plant according to [30], wherein the receptor-like kinase RLK gene has a cDNA sequence comprising a nucleotide sequence as set forth in SEQ ID NO:1, and the gene homologous to the receptor-like kinase RLK gene has a cDNA sequence comprising a nucleotide sequence which has at least 85% homology to the nucleotide sequence as set forth in SEQ ID NO:1.

[32] The method for producing a virus resistant solanaceous plant according to [31], wherein the mutation is introduced into the receptor-like kinase RLK gene or the gene homologous thereto at a region corresponding to a nucleotide sequence as set forth in SEQ ID NO:3.

[33] The method for producing a virus resistant solanaceous plant according to [32], wherein the mutation is introduced so that the region corresponding to the nucleotide sequence as set forth in SEQ ID NO:3 is changed to a nucleotide sequence as set forth in SEQ ID NO:8 or 9.

[34] The method for producing a virus resistant solanaceous plant according to any one of [27] to [33], wherein the solanaceous plant is tomato.

[35] A virus resistant solanaceous plant obtained by the production method according to any one of [27] to [34].

In addition, the present invention provides the following method for producing a bred progeny of a solanaceous plant and a solanaceous plant obtained by the production method.

[36] A method for producing a bred progeny of a virus resistant solanaceous plant which is resistant to tomato spotted wilt virus, the method comprising: self-pollination or cross-pollination of either a virus resistant solanaceous plant obtained by the production method according to any one of [27] to [34] or a progeny of the virus resistant solanaceous plant.

[37] A virus resistant solanaceous plant resistant to tomato spotted wilt virus, the solanaceous plant being obtained by the production method of [36].

Advantageous Effects of Invention

According to the present invention, there is provided a virus resistant solanaceous plant, a solanaceous plant cell, and a method for producing the solanaceous plant, in which the solanaceous plant has inhibitory properties against: infection by TSWV, propagation of TSWV, and/or expression of TSWV symptoms.

BRIEF DESCRIPTION OF DRAWINGS

FIG. 1 is tomato receptor-like kinase RLK gene (solyc02g091840) in which a single underlined portion is exon 1, a double underlined portion is a guide RNA recognition site (790th nucleotide to 809th nucleotide of exon 1), and a portion enclosed in a box is PAM sequence;

FIG. 5 is a drawing showing nucleotide sequences of the mutated regions of the RLK mutated lines, wherein FIG. 6 is a drawing showing mutation patterns in the tomato receptor-like kinase RLK gene.

DESCRIPTION OF EMBODIMENTS

Figure 2:
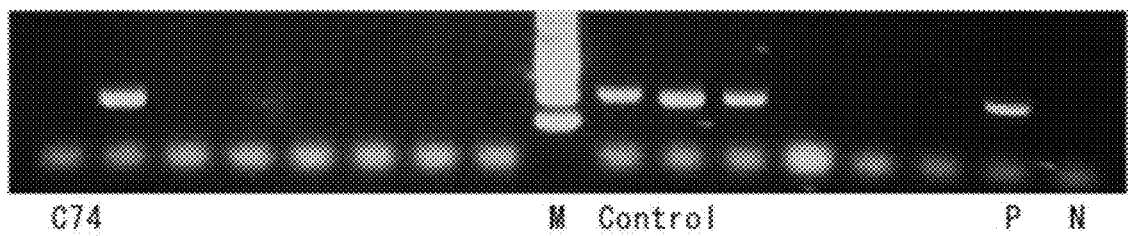
FIG. 2 is an electropherogram showing the results of reverse transcription PCR (hereinafter, abbreviated to "RT-PCR") analysis of the first TSWV inoculation test.

Present inventors have conducted extensive and intensive studies for solving the above-mentioned problems, and found that, when solanaceous plants have a mutation in receptor-like kinase RLK gene or a gene homologous thereto, and the mutation either inhibits expression of the mutated RLK gene or makes a protein encoded by the mutated gene to be non-functional for TSWV, the solanaceous plants have virus resistance against TSWV. This is a first report on TSWV resistant plant among the solanaceous plants.

Embodiments of the present invention (hereinafter, may be referred to as "present embodiment") are explained in detail below. The present invention is not limited to the present embodiments and the drawings, and may be practiced with various changes within the scope of the gist of the present invention.

[I] TSWV Resistant Solanaceous Plant

In one aspect, the present embodiment relates to a TSWV resistant solanaceous plant. In the present embodiment, the TSWV resistant solanaceous plant is a plant having the properties of inhibiting the infection of TSWV, suppressing the propagation of TSWV when infected, and/or suppressing the expression of TSWV symptoms. The TSWV resistant solanaceous plant is preferably a plant having a property of inhibiting the TSWV infection, or when infected, inhibiting the propagation of TSWV.

In the present embodiment, there is no particular limitation with respect to the solanaceous plants as long as the plants belongs to the family Solanaceae, and such plants include those belonging to the genus *Solanum*, genus *Nicotiana*, genus *Capsicum* or the like. Specific examples of such plants include tomato (*Solanum lycopersicum*), eggplant (*Solanum melongena*), tobacco (*Nicotiana tabacum*), hot pepper (*Capsicum annuum*), potato (*Solanum tuberosum*) and the like, and the plants are preferably tomato, eggplant or potato, and more preferably tomato.

(RLK Gene)

The TYLCV resistant solanaceous plants of the present embodiment have a mutation in the receptor-like kinase RLK gene or a gene homologous thereto.

The RLK gene is a tomato gene encoding "Receptor-Like Kinase," that is a kinase resembling a receptor. RLK is called BAM1 (Barely Any Meristem 1) in Arabidopsis and the gene encodes CLAVATA1 related receptor-like kinase protein necessary for meristematic functions of shoots and flowers which are related to the formation of leaves and gametes. Further, in Arabidopsis, presence of BAM2 which is highly homologous to BAM1 has been recognized, and from recent studies, presence of a highly homologous homologue in tomato is beginning to be understood. When the RLK used in the present embodiment is the "RLK1" (Solyc02g091840 on chromosome 2), such a homologue is a protein known as "RLK2." Regarding BAM1 of Arabidopsis, although relationship with C4 protein of viruses of the family Geminiviridae and genus *Begomovirus*, and involvement in replication of a closely related virus have been suggested, till now, there is no report on a relationship between tomato RLK and *Tospovirus* including TSWV.

In the present embodiment, the "RLK gene" is preferably a gene having a cDNA sequence which either comprises the nucleotide sequence as set forth in SEQ ID NO:1, or consists of the nucleotide sequence as set forth in SEQ ID NO:1.

In the present embodiment, the "gene homologous to the RLK gene" is preferably a gene having a cDNA sequence which either comprises a nucleotide sequence which has sequence homology to the nucleotide sequence as set forth in SEQ ID NO:1, or consists of a nucleotide sequence which has sequence homology to the nucleotide sequence as set forth in SEQ ID NO:1. There is no particular limitation on the degree of sequence homology with the nucleotide sequence as set forth in SEQ ID NO:1, but the sequence homology is preferably at least 85% and less than 100%.

Minimum sequence homology may be any value, such as at least 87%, at least 90%, at least 93%, at least 95%, at least 97%, at least 99%, and at least 99.5%. Homology between the nucleotide sequence as set forth in SEQ ID NO:1 and the cDNA sequence of the homologous gene may be determined by conventional methods. For example, homology between nucleotide sequences may be determined using conventional homology search programs, such as BLAST.

(TSWV Resistance Gene)

In the present embodiment, the solanaceous plants have a mutation in at least one gene selected from the group consisting of the receptor-like kinase RLK gene and a gene homologous thereto (hereinafter, a gene having a mutation is also referred to as a "TSWV resistance gene"). The mutation either inhibits the expression of the mutated gene or makes a protein encoded by the mutated gene to be non-functional for TSWV. The protein which is non-functional for TSWV refers to either a protein which cannot be used by TSWV during its infection and replication, or a protein which reduces the infection and replication of TSWV. In one aspect, the TSWV resistance gene may be a gene which has been mutated to no longer encode a protein.

Although not bound by any theory, during plant infection, TSWV is considered to use a specific RLK isoform among the plurality of RLK isoforms present in a solanaceous plant. When a gene encoding the specific isoform used by TSWV (i.e., RLK functional for TSWV) has a mutation, and the mutation either prevents the production of the specific RLK protein used by the TSWV or causes the produced RLK protein to be non-functional for TSWV, progression of translation of proteins required for virus infection and propagation which are encoded by the viral genome is likely to be blocked. Alternatively, the infection and propagation of TSWV may be inhibited due to incomplete function of TSWV proteins which needs an interaction with the RLK protein. These manners are considered to confer TSWV resistance to Solanaceous.

On the other hand, even when one of the plurality of RLK homologues present in the solanaceous plant becomes mutated, the plant itself is capable of using other homologues, or the plant itself is capable of using the RLK protein non-functional for TSWV. Accordingly, TSWV resistance can be conferred to the plant without causing adverse effects on the growth of host solanaceous plant. Specifically, the presence of RLK2 highly homologous to RLK1 (Solyc02g091840 on chromosome 2) is known, and the two RLKs are considered to exist in plants while assisting each other.

As explained above, the solanaceous plants having the TSWV resistance gene acquire TSWV resistance. For example, a plant may be judged as having the "TSWV resistance" when the amount of accumulated TSWV in a plant body on day 20 or more post TSWV inoculation is the same or less than the amount in a plant without TSWV inoculation, and/or when symptoms of TSWV infection cannot be observed visually on day 20 or more post TSWV inoculation. Specifically, as shown in the below-mentioned Examples, TSWV resistance of plants may be judged by: infecting plants with TSWV using a routine procedure, and determining the amount of TSWV accumulation in plant bodies by conventional methods, such as ELISA, RT-PCR, and the like. In addition, TSWV resistance of plants may be judged by observation of the presence or absence of TSWV symptoms (mosaic pattern and yellowing of leaves, fern leaves, dwarfing, necrosis, etc.) on the TSWV infected plants.

As long as the solanaceous plants have the above-mentioned TSWV resistance, the gene mutation may be present in at least one gene selected from the group consisting of the receptor-like kinase RLK gene and a gene homologous thereto. Therefore, the present embodiment includes solanaceous plants having a mutation in the receptor-like kinase RLK gene and/or the gene homologous thereto.

Further, when the TSWV resistant solanaceous plants of the present embodiment have a mutation in the RLK gene, the plants may have mutations in all of the genes each encoding the RLK protein which is functional for TSWV. For example, in the case of diploid plants, such as amphidiploid plants, each of the plurality of genes encoding the RLK protein functional for TSWV preferably has a mutation therein. As long as the TSWV resistant solanaceous plants have a mutation in a gene encoding the RLK protein functional for TSWV, the TSWV resistant solanaceous plants may have other normal RLK gene(s). Further, the TSWV resistant solanaceous plants may be plants in which endogenous gene(s) encoding the RLK protein functional for TSWV have been made non-functional due to complete loss, damage or the like, but instead, containing an introduced exogenous RLK gene.

In other words, all of the genes encoding any one of the proteins which are functional for TSWV may have the mutation and, preferably, all of the genes encoding the proteins functional for TSWV have the mutation. As long as such TSWV resistant solanaceous plants have a mutation in a gene encoding any one of the proteins which are functional for TSWV, the TSWV resistant solanaceous plants may have other normal gene(s). Further, the TSWV resistant solanaceous plants may be plants in which the endogenous gene(s) encoding the protein functional for TSWV have been made non-functional due to complete loss, damage or the like, but instead, containing an introduced exogenous homologous gene(s).

In one aspect of the present embodiment, the TSWV resistant solanaceous plants have a mutation in their genomic gene. Specific examples of such a gene mutation include mutations (a) to (d) below:

(a) a frameshift mutation, (b) a nonsense mutation, (c) a loss of continuous or non-continuous 3n nucleotides (wherein n=1 to 7), and (d) a replacement, deletion, addition, and/or insertion of 1 or more nucleotides.

(a) The frameshift mutation is a mutation where a loss or addition of a nucleotide causes a shift in a reading frame of a codon and the mutated gene encodes a different amino acid sequence. Due to the change in the encoded amino acid sequence, the mutated gene becomes a TSWV resistance gene.

(b) The nonsense mutation is a mutation where a codon intrinsically encoding an amino acid is changed to a termination codon, and due to this change, the mutated gene becomes a TSWV resistance gene.

(c) The loss of continuous or non-continuous 3n nucleotides (wherein n=1 to 7, preferably n=1 to 3, for example, the 3n nucleotides are 3, 6 or 9 nucleotides) results in a change in the amino acid sequence encoded downstream of this lost region. Due to the occurrence of such a change, the mutated gene becomes a TSWV resistance gene.

(d) The replacement, deletion, addition, and/or insertion of 1 or more nucleotides results in a change in a reading frame of an amino acid sequence encoded by a nucleotide sequence downstream of the mutated region. The change in the reading frame results in a change in intrinsically encoded amino acid sequence, and this causes a conformational change and the like of the encoded protein and the mutated gene becomes a TSWV resistance gene. In one aspect, this mutation is preferably a mutation of a nucleotide other than the 3rd nucleotide of a codon. There is no particular limitation on the number of replaced, deleted, added, and/or inserted nucleotides as long as the TSWV resistance gene is obtained. For example, the number of nucleotides may be 1 to 5, 1 to 3, or 1 to 2.

The mutation of the TSWV resistance gene is preferably at least one mutation selected from (a) to (d) above. The above-mentioned mutations (a) to (d) are not alternatives; for example, there are cases where the mutation (a) or (b) occurs as a result of the mutation (c) or (d).

There is no particular limitation with respect to the mutation in the genome of the solanaceous plants as long as the mutation inhibits the gene expression of the mutated gene or makes the protein encoded by the mutated gene to be non-functional for TSWV, and imparts TSWV resistance to the plants and also causes no considerable damage to the life or growth of the plants.

Next, the mutations are explained in detail.

In one aspect, when the solanaceous plants have a mutation in the RLK gene, the mutation is preferably in exon 1 (SEQ ID NO:2) of the RLK gene, and more preferably in a region comprising the 790th to 809th nucleotides in exon 1, that is, the region comprising TCTCTAGAGTACCTTGCAGT as set forth in SEQ ID NO:3. When the solanaceous plants have mutation in the gene homologous to the RLK gene, the mutation is preferably in a region of the homologous gene which corresponds to the nucleotide sequence as set forth in SEQ ID NO:2, and more preferably in a part of the above region which corresponds to the nucleotide sequence as set forth in SEQ ID NO:3.

When the solanaceous plants have a mutation in the sequence TCTCTAGAGTACCTTGCAGT as set forth in SEQ ID NO:3 or a region corresponding to the sequence, the mutation is preferably a deletion of 5 nucleotides, or insertion of 1 nucleotide. Nucleotide sequences of regions with such mutations are shown in SEQ ID NOs:8 and 9 and FIGS. 5 and 6. Further, the nucleotide sequence of the RLK gene with 5 nucleotide deletion is shown in SEQ ID NO: 10, and the nucleotide sequence of the RLK gene with 1 nucleotide insertion is shown in SEQ ID NO: 11.

It should be noted that the mutations in the solanaceous plants are not limited to the above-mentioned regions, and mutations may exist in other regions of the RLK gene, and other genes, as long as TSWV resistance is maintained.

In one aspect, the mutation in the gene of the solanaceous plants is preferably a genomic gene mutation introduced by genome editing techniques, such as the below-mentioned CRISPR system.

The mutated gene in the genome may be homozygous in which the mutation exists in both alleles, or heterozygous in which the mutation exists in one of the alleles, but homozygous mutation is preferred. This is because properties imparted by the mutated gene are more strongly exhibited by a homozygous mutation in which both alleles are characterized by the same mutated sequence.

(TSWV Resistant Solanaceous Plant and Parts Thereof)

The TSWV resistant solanaceous plants of the present embodiment may be solanaceous plants with complex resistance, i.e., showing resistance against bacteria and viruses other than TSWV, as long as the plants show resistance against TSWV. Specific examples of other viruses include all *Potyviruses* (PVY, etc.); viruses belonging to the genera *Bymovirus* and *Sobemovirus* and having a VPg similar to that of the PVY at their 5' terminus, in which a mutation in a translation initiation factor has been reported to impart resistance against these viruses; and viruses belonging to the genus *Carmovirus* in which a mutation in a translation initiation factor has been reported to impart resistance against these viruses.

In one aspect, the present embodiment relates to parts of the TSWV resistant solanaceous plants. Such parts include not only parts collected from the solanaceous plants having the above-mentioned characteristics, and their progenies or clone plants, but also derivatives obtained from plant bodies or parts thereof. Specific examples of the parts include organs, such as fruits, shoots, roots, burgeons, and anthers; and plant tissues and cells. The parts may take any form, such as a suspension culture, protoplast, germ, callus tissue, lamina, gametophyte, sporophyte, pollen or microspore. An example of a derivative of the solanaceous plant is seeds.

In the present embodiment, the part of the TSWV resistant solanaceous plants may be a scion, rootstock, etc. used for grafting. Further, in one aspect, the present embodiment relates to plant cells (including callus) which can regenerate the above-mentioned TSWV resistant solanaceous plants, and the TSWV resistant solanaceous plants of the present embodiment also include such plants obtained from plant cells.

Parts of the solanaceous plants having TSWV resistance are preferably fruits which are edible fresh or useful for processing. In addition, the parts are preferably seeds which are useful for progeny production and the like.

(Processed Material of Solanaceous Plants or Parts Thereof)

In one aspect, the present embodiment relates to a processed material of the solanaceous plants or the parts thereof. There is no particular limitation with respect to the processed materials, and examples include edible, industrial, and medical processed materials, and preferably the processed materials are edible materials.

For example, when the solanaceous plant having TSWV resistance is a tomato, examples of edible processed materials of tomato include canned tomatoes, tomato pastes, ketchups, tomato sauces, tomato soups, dried tomatoes, tomato juices, tomato powders, and tomato concentrates. A nutritional supplementary food (supplement) made from tomatoes is also an example of a processed material.

[II] Solanaceous Plant Cells Having TSWV Resistance

In one aspect, the present embodiment relates to Solanaceous plant cells having TSWV resistance.

The solanaceous plant cells of the present embodiment has a mutation in at least one gene selected from the group consisting of the receptor-like kinase RLK gene and a gene homologous thereto. Details of these genes and their mutation are already explained above in connection with the TSWV resistant solanaceous plants.

TSWV resistance of the solanaceous plant cells may be confirmed by the above-mentioned methods. For example, absence or presence of TSWV resistance can be confirmed by infecting plant cells with TSWV using a routine procedure, and determining the amount of TSWV accumulation in plant cells by conventional methods, such as ELISA, RT-PCR, and the like.

The TSWV resistant solanaceous plant cells of the present embodiment may be either cells isolated from the above-mentioned solanaceous plants and their progenies or clone plants, or plant cells with introduced gene mutation which are obtained by the below-mentioned method for producing a TSWV resistant solanaceous plant. Further, there is no particular limitation on the form of the plant cells, and the plant cells include a suspension culture and protoplast.

There is no particular limitation on the type of plant cells as long as the cells are solanaceous plant cells. The cells are preferably the cells of tomato, eggplant, tobacco, hot pepper, or potato, and more preferably the cells of tomato, eggplant or potato, and most preferably the cells of tomato.

In one aspect, the present embodiment relates to solanaceous plant bodies and parts thereof containing the above-mentioned solanaceous plant cells and having TSWV resistance. The solanaceous plant bodies and parts thereof include plant bodies or parts, such as tissues and organs, which have been regenerated from plant cells carrying an introduced gene mutation. Parts of a plant body regenerated from plant cells are also parts containing the above-mentioned solanaceous plant cells. The details of the parts are the same as those mentioned above in connection with the TSWV resistant solanaceous plants.

Further, parts of the solanaceous plants are preferably fruits which are edible fresh or useful for processing. In addition, the parts are preferably seeds which are useful for progeny production and the like.

In one aspect, the present embodiment relates to a processed material of the solanaceous plants or the parts thereof. There is no particular limitation with respect to the processed materials, and examples include edible, industrial, and medical processed materials, and preferably the processed materials are edible materials.

[III] Method for Producing a TSWV Resistant Solanaceous Plant

In one aspect, the present embodiment relates to a method for producing a TSWV resistant solanaceous plant. Specifically, the method comprises the following steps:

selecting at least one gene from the group consisting of the receptor-like kinase RLK gene and a gene homologous thereto;

introducing a mutation into the selected gene in a genome, in which the introduced mutation is either a mutation inhibiting an expression of the mutated gene or a mutation making a protein encoded by the mutated gene to be non-functional for TSWV; and selecting a solanaceous plant having resistance to TSWV.

Firstly, a target gene for introducing a mutation is selected. At least one gene is selected from the group consisting of the receptor-like kinase RLK gene and a gene homologous thereto. The selected gene may be single gene or a combination of two or more genes. Details of the genes are the same as those explained above in connection with the TSWV resistant solanaceous plants.

Secondly, a mutation is introduced into the selected gene. Methods for introducing a mutation into a genomic gene can be broadly classified into two methods exemplified below.

(1) Direct genome editing: A method in which a plant carrying a TSWV resistance gene is produced by directly editing a plant genome carrying the RLK gene functional for TSWV to introduce a mutation into a desired site at a pin point.

(2) Introduction of mutated gene: A method which combines the following steps (A) and (B): (A) TSWV resistance gene is produced, and introduced into a plant by using an appropriate promotor; and (B) among endogenous genes of a plant which correspond to the TSWV resistance gene produced in step (A) above, a gene functional for TSWV is changed into a gene non-functional for TSWV.

Each method is explained below.

(1) Direct Genome Editing

Direct genome editing can be performed using conventional genome editing techniques which use a site specific nuclease, such as CRISPR, TALEN or the like. When a double strand cleavage is introduced using a restriction enzyme capable of cleaving a specific site in a genome, various mutations are introduced at the time of repair due to a repair error. As a result, a mutation is introduced into a target gene (in the present embodiment, a gene encoding RLK functional for TSWV).

Preferably a CRISPR system, and more preferably a CRISPR/Cas9 system is used since these systems are capable of introducing mutation at high specificity and high efficiency. In the CRISPR/Cas9 system, a guide RNA (sgRNA) which has a sequence of about 20 nucleotides long and which is homologous to the target gene recognizes the target and Cas9 protein cleaves the double strand. During the repair of the resultant cleavage by non-homologous end-joining (NHEJ) repair cycle, a mutation is introduced into the target site due to a repair error.

Delivery of the Cas9 protein and sgRNA to a plant may be performed via a vector encoding the same by using methods well-known to those skilled in the art, such as an agrobacterium method, a standard transfection, electroporation, particle bombardment and the like.

Briefly, as explained in Examples hereinbelow, the Cas9 protein and sgRNA are delivered to plants by constructing a binary vector with incorporated Cas9 gene and sgRNA, and transforming agrobacterium with the constructed vector, followed by transformation of plants with the agrobacterium (see, for example, Friedrich Fuser et al., "The Plant Journal," 2014, 79: 348-359; and Ryo Oosawa and Hiroshi Ezura, "Atarashii Shokubutu Ikushu Gijyutu wo Rikaisiyou—NBT (New plant breeding techniques) (Understanding New Plant Breeding Techniques—NBT (New plant breeding techniques))", International Academic Publishing Co., Ltd., 2013).

There is no particular limitation on the form of the plants being transformed with the agrobacterium, as long as the plant is capable of regenerating a plant body. Examples of such plant forms include a suspension culture, protoplast, leaf explants, callus and the like. After removing the agrobacterium, the transfected plants can be cultured in a medium containing a drug selected in accordance with the vector used, and a selection culture of a plant (explants) having an incorporated desired gene may be performed based on drug resistance.

The guide RNA may be designed to enable a highly efficient introduction of a mutation into a target site. In general, a site which is three nucleotides upstream of a 3-nucleotide sequence called a PAM sequence (which is NGG for the most popular Cas9 derived from *S. pyogenes*) is basically cleaved in a CRISPR system. Since the PAM sequence must exist immediately after the target sequence, the guide RNA may be designed so that the target sequence is located upstream of the PAM sequence.

When designing the guide RNA, GC content is preferably taken into consideration because higher the GC content, the higher is the cleavage efficiency. Further, the system may be designed to minimize non-specific cleavage by an off-target effect.

In FIG. 1 which illustrates the cDNA sequence (SEQ ID NO:1) of the RLK gene present on chromosome 2 of a tomato, the guide RNA may be designed so that the PAM sequence is the boxed portion in exon 1 (underlined portion of FIG. 1; SEQ ID NO:2) and the target is generally 20 nucleotides (SEQ ID NO:3) located upstream of the boxed 3 nucleotides. The direct genome editing of other solanaceous plants can be performed in the same manner as in tomatoes, by selecting a target from a region in a gene homologous to the RLK gene which corresponds to the nucleotide sequence as set forth in SEQ ID NO:3 and, then, selecting the PAM sequence and designing the guide RNA. Plants having TSWV resistant RLK gene can be produced by introducing a mutation into the target site in the above-mentioned manner.

When a double strand cleavage is introduced into a single site by the CRISPR system, about 20 nucleotides are repaired and a mutation is considered to be introduced by the repair error. Therefore, in one aspect, the mutation in the TSWV resistance gene of the present embodiment is a mutation of continuous or non-continuous 3n nucleotides (wherein n=1 to 7, preferably n=1 to 3).

Further, the present embodiment relates to the guide RNAs and vectors comprising the guide RNA which are used for producing the TSWV resistant solanaceous plant. The sequences of the guide RNAs are as mentioned above. The present embodiment also relates to kits comprising the guide RNA. The kits may comprise a site specific nuclease and the like which are necessary for genome editing using the CRISPR system, and the kit may be used for producing the TSWV resistant solanaceous plants.

(2) Introduction of Mutated Gene

Introduction of mutated gene is a method which combines the following steps (A) and (B).

(A) TSWV resistance gene is produced, and introduced into a plant by using an appropriate promotor; and (B) among endogenous genes of a plant which correspond to the TSWV resistance gene produced in step (A) above, a gene functional for TSWV is changed into a gene non-functional for TSWV.

There is no particular limitation on the order for performing the above steps (A) and (B) as long as the steps cause no fatal damage to the plants, and step (B) may be performed before step (A). It should be noted that a method which performs step (B) alone at a specific part of the plant is the method (1) Direct Genome Editing.

In step (A), a mutated gene encoding RLK protein non-functional for TSWV is produced and introduced into plants using an appropriate promotor. Production of the mutated gene may be performed by conventional methods well-known in the art. For example, a nucleotide sequence having a desired mutation may be synthesized and amplified by PCR, etc. The mutations introduced herein are the same as those explained above in connection with the TSWV resistant solanaceous plants.

Introduction of the produced mutated gene into plants may be also performed by conventional methods well-known in the art. In brief, the introduction may be performed using a vector containing the mutated gene, for example by a polyethylene glycol method, electroporation, agrobacterium method, particle gun method and the like. The mutated gene introduced herein is the TSWV resistance gene obtained by introducing a mutation into the RLK gene (or the gene homologous thereto) derived from a solanaceous plant, and the TSWV resistance gene can be derived from solanaceous plants of different species.

There is no particular limitation on the form of the plants used for introducing the above-mentioned vector, as long as the plant is capable of regenerating a plant body. Examples of such plant forms include a suspension culture, protoplast, leaf explants, callus and the like.

Next, in step (B), among the endogenous RLK gene (or the gene homologous thereto) of the plant, a gene which is functional for TSWV is changed into a gene which is non-functional for TSWV. Step (B) may be performed using conventional methods which are used for introducing mutation into plants. Examples of such methods include treatments with a mutagen, such as ion beam or EMS (Ethyl methanesulfonate). Step (B) may be performed using the above-mentioned genome editing techniques, such as CRISPR and TALEN. Desirably, all of the genes functional for TSWV among the endogenous RLKs are changed into a state which is non-functional for TSWV.

Subsequently, a plant body is regenerated from the parts (such as, leaf explants or plant cells) of the plant carrying the TSWV resistance gene. Regeneration of the plant body may be performed by well-known conventional methods in accordance with the type of the plant. For example, regeneration may be performed by making reference to Sun H. J. et al., "Plant Cell Physiol.," 2006, 47: 426 and the like for tomatoes, and Jefferson R. A. et al., "EMBO J.," 1987, 6:3901 and the like for tobaccos.

Further, solanaceous plants having resistance against TSWV are selected from the regenerated plants. Such a selection may be performed by the above-mentioned methods for confirming TSWV resistance. For example, plants having TSWV resistance may be selected by infecting the plants with TSWV using a routine procedure and determining the amount of TSWV accumulation in the plants by conventional methods, such as ELISA, RT-PCR and the like. Alternatively, solanaceous plants having TSWV resistance may be selected by observation of the presence or absence of TSWV symptoms (mosaic pattern and yellowing of leaves, fern leaves, dwarfing, necrosis, etc.) on the TSWV infected plants.

The solanaceous plants produced by the above-mentioned methods include tomato, eggplant, tobacco, hot pepper, potato and the like, preferably tomato, eggplant, and potato, and more preferably tomato.

In one aspect, the present embodiment relates to solanaceous plants produced by the above-mentioned method. Such solanaceous plants are the same as the TSWV resistant solanaceous plants explained above.

Once the TSWV resistant solanaceous plants carrying the TSWV resistance gene are obtained, progenies and clones of such plants may be obtained by conventional methods. Therefore, the TSWV resistant solanaceous plants of the present embodiment include such progenies and clones.

In one aspect, the present embodiment relates to a method for producing a bred progeny of the TSWV resistant solanaceous plant, comprising: self-pollination or cross-pollination of TSWV resistant solanaceous plant (first generation) or its progeny. The self-pollination or cross-pollination of a plant can be performed by any conventional methods well-known in the art and can be performed under either natural or artificial conditions. The progeny obtained in this manner may be subjected to self-pollination or cross-pollination to produce a further progeny.

Recessive resistance may not show immunological resistance like dominant resistance, and sometimes there is a possibility of permitting virus infection or transfer and propagation. However, unlike dominant resistance which bring resistance into effect by the ligand-receptor reaction between a specific gene of a virus and a specific gene of a plant, the recessive resistance suppresses the infection rate drastically by preventing the virus from using a host factor necessary for viral infection and proliferation. The recessive resistance is considered to well-qualified for sustainable breeding from an aspect different from that of the dominant resistance in which the resistance can be broken by a small mutation in the virus.

EXAMPLES

<Preparation of Mutants>

Example 1

Production of Recombinant *Agrobacterium* for Introducing Mutation Into RLK Gene:

Guide RNA recognition site was designed in exon 1 (SEQ ID NO:2) of RLK gene (Solyc02g091840) which is said to be present on chromosome 2 of tomatoes. Double stranded DNA corresponding to the designed 20 nucleotide-long site (SEQ ID NO:3: TCTCTAGAGTACCTTGCAGT) was synthesized and inserted into restriction enzyme BbsI site of vector pUC19_AtU6oligo (obtained from National Research and Development Agency, National Institute of Agrobiological Sciences), thereby constructing a recombinant vector. cDNA sequence of the RLK gene present on chromosome 2 of wild-type tomatoes is shown in FIG. 1 and SEQ ID NO:1.

A cassette site containing the guide RNA region was cutout from the constructed recombinant vector and inserted into restriction enzyme I-SceI site of binary vector pZD_OsU3gYSA_HolgerCas9_NPTII, thereby obtaining a recombinant binary vector. *Agrobacterium* LBA4404 (manufactured and sold by TAKARA BIO® INC.) was transformed with the binary vector by a standard method to obtain a recombinant agrobacterium.

Example 2

Transformation of Tomatoes:

A conventional variety Moneymaker and a personal variety S were used for transformation of tomatoes. Transformation of tomatoes using an agrobacterium was performed in accordance with a common textbook (for example, Yataka Tabei ed., "Keishitutenkan Purotokoru<Shokubutu-hen> (Protocols for plant transformation)", Kagaku-Dojin Publishing Company, INC., 2012). Specifically, either explants of cotyledons obtained by germination of tomato seeds in sterile medium, or sterilized explants of cotyledons or leaves obtained by usual seeding were prepared. Next, the recombinant agrobacterium obtained in Example 1 was cultured until the turbidity of the culture liquid reached 0.1 to 1.0, and the leaf explants were immersed in the culture liquid for about 10 minutes, to thereby infect the explants with the agrobacteria.

On day 3 post infection, the agrobacterium was removed. Tomato leaf explants were transferred to Murashige and Skoog medium (may be abbreviated to MS basic medium) (a medium obtained by adding 3% sucrose, 1.5 mg/L zeatin and 1% agar to MS basic medium) supplemented with carbenicillin (100 to 500 mg/ml) and kanamycin (20 to 100 mg/ml). The leaf explants were subjected to selection culture at 25° C. under light (16 hours light/8 hours dark). Leaf explants were transferred by changing the medium every 10 days to 2 weeks from the start of the culture, thereby promoting the formation of callus from the leaf explants. The transferring and selection were continued further to induce the formation of adventitious buds.

When the size of the adventitious buds reached several centimeters, the buds or shoots were transferred to a rooting medium (a medium obtained by adding 1.5% sucrose, 1% agar, 50 to 250 mg/ml carbenicillin, 20 to 100 mg/ml kanamycin, and optionally naphthalene acetic acid (NAA), to MS basic medium) and cultured for 1 to 3 months while passaging every month.

All cultures, up to the culture in the rooting medium, were sterile cultures. The rooted plants were taken out from the sterile medium and transferred to a conventional pot soil obtained by mixing black soil, Akadama soil and the like, and cultivated in the pot. The thus obtained regenerated plants were first generation transgenic plants (hereinbelow, sometimes abbreviated to "T0").

Example 3

Selection of Gene-Edited Line:

For confirming the presence or absence of gene recombination and edited site (site with deletion, insertion or replacement of a nucleotide) in the target gene of the first generation transgenic plants, the desired sites were amplified by PCR using the following primers: Primer 1 (TTAACACGTCTGCGTAACCTC (SEQ ID NO:4)), and Primer 2 (CCGGTGAAGGTATTGTAGTATCC (SEQ ID NO:5)) for the region in the RLK (Solyc02g091840).

PCR was performed using the PCR enzyme "KOD Plus Neo®" manufactured and sold by TOYOBO® CO., LTD., and DNA was amplified in accordance with the enclosed manual.

Next, the amplified fragments were treated with a restriction enzyme having its cleavage site in the target site of the fragments to confirm whether the amplified fragments are cleaved by the restriction enzyme or not. Specifically, XbaI was used. Amplified fragments will not be cleaved by the restriction enzyme when the restriction site is changed by recombination and editing of the gene. Occurrence of gene recombination and editing in the target gene was determined based on the non-cleavage of the amplified fragments (data not shown).

As a result, in some of the regenerated plants, editing of a sequence in the RLK gene was confirmed and edited lines were selected. The selected RLK-edited line was named C74 line.

Plants (T0) of the selected, gene-edited line were grown in an isolated green house and were self-pollinated for collecting seeds, and transgenic progeny (T1) seeds were collected. The T1 plants were further self-pollinated for collecting seeds, and the collected progeny seeds were the T2 generation.

Example 4

<TSWV Inoculation Test>
Method:

The T2 generation seeds of the C74 line, the RLK-edited line obtained in Example 3, were sowed to obtain tomato seedlings about 10 cm in height. The obtained tomato seedlings were mechanically inoculated with a ground crude juice of TSWV infected leaves. The ground crude juice of the TSWV infected leaves (also called virus crude juice) was obtained by inoculating and proliferating TSWV in *Nicotiana rustica* (Tobacco), collecting infected leaves which started to show necrotic spots, freezing the leaves at –80° C., grounding 0.5 g of the frozen leaves in 0.05M phosphate buffer (pH7.0, containing 10 mM sodium sulfite), and diluting by 10- to 20-fold. The mechanical inoculation was performed by soaking a cotton swab in the virus crude juice and rubbing on the virus crude juice with celite (No. 454) to the first or second true leaf of the tomato plant. Strain S8 which is a wild strain (WT) before mutation was used as a control plant.

Fifteen to thirty days after the above-mentioned inoculation of the virus crude juice, inoculated leaves and upper leaves were visually observed for disease symptoms. Specifically, occurrence of mosaic pattern, yellowing, and necrosis was scored positive.

In addition, leaves (about 0.1 g each) close to the growing point was sampled and total RNA was extracted therefrom using PLANT TOTAL RNA mini kit (manufactured and sold by VIOGENE™). Using the total RNA as a template, cDNA was synthesized by reverse transcription using Primescript™ II 1ST Strand cDNA synthesis kit (manufactured and sold by TAKARA BIO® INC.), and amplification products were obtained by PCR (Conditions: 2 minutes at 95° C.; 31 cycles of 30 seconds at 94° C., 40 seconds at 56° C., and 45 seconds at 72° C.; and 3 minutes at 72° C.) by using *Tospovirus* detection primer 3 (5'-CTGTARTGKTC-CATWGCARCA (SEQ ID NO:6)) and primer 4 (5'-GAYATGACYTTCMGAAGRCTTGAT (SEQ ID NO:7)) and GO Taq® Green master polymerase (manufactured and sold by Promega® Corporation). The primers were based on consensus sequence for Tospoviruses. The obtained amplification product was subjected to 1% agarose gel electrophoresis to confirm the infection with TSWV.

The above test was repeated 3 times. In the first test, observation for disease symptoms and RT-PCR were performed 25 days after inoculation; in the second test, observation for disease symptoms and RT-PCR were performed 27 days after inoculation; and in the third test, only the observation for disease symptoms was performed 25 days after inoculation.

Results

Figure 3:
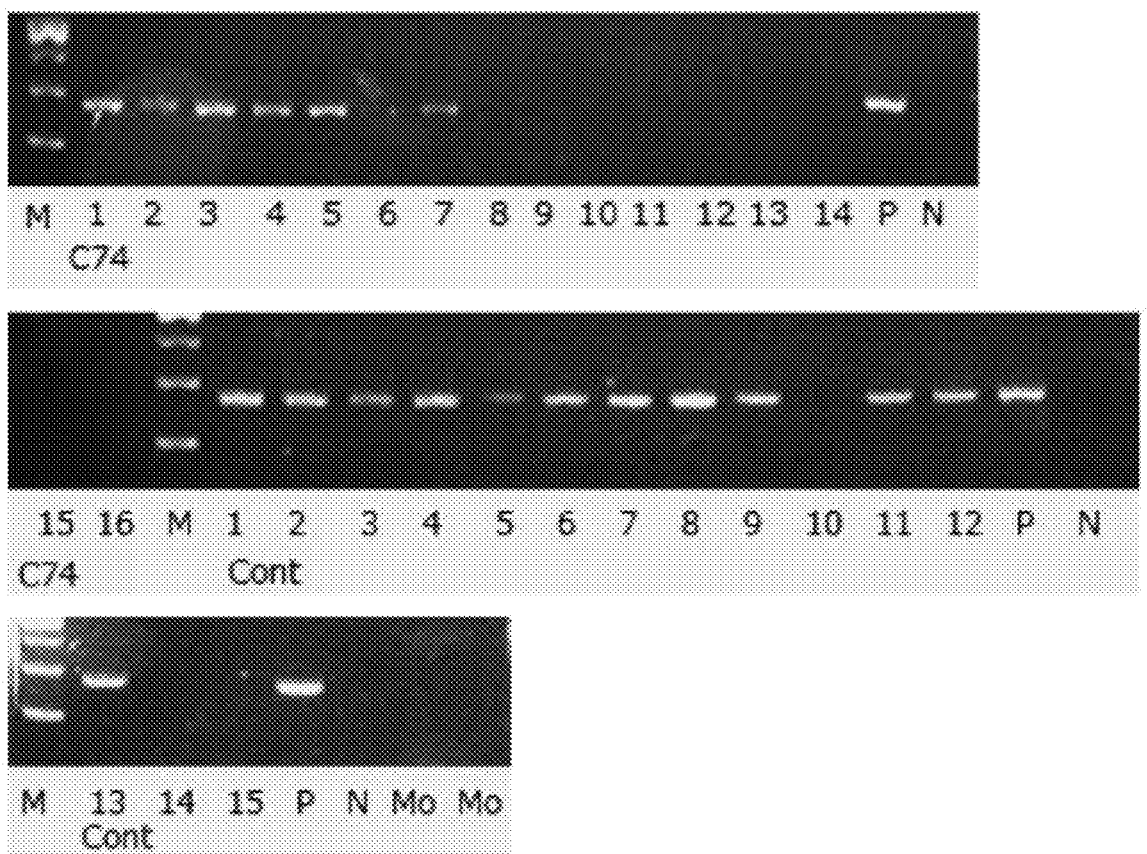
FIG. 3 is an electropherogram showing the results of RT-PCR analysis of the second TSWV inoculation test.
Figure 4:
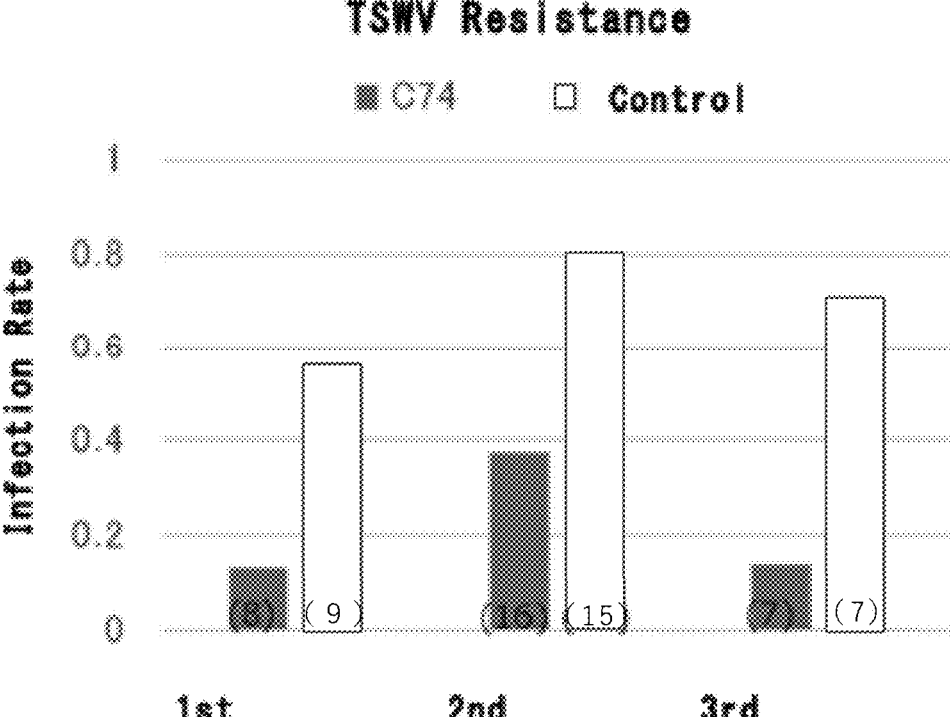
FIG. 4 is a graph showing virus morbidities obtained in the 1st, 2nd and third TSWV inoculation tests of RLK mutated line, and the number in ( ) is the number of samples.

FIG. 2 shows the results of RT-PCR in the first test for the C74 line and the control, i.e., wild-type tomato without mutation. In the drawing, M represents molecular weight marker, P represents positive control, and N represents negative control, lanes at the left of M are the C74 line, and lanes at the right of M are the control. Leaves without any symptoms were basically used as the control, but leaves with the symptoms were arbitrary analyzed. In FIG. 2, the upper band shows the presence of the virus. In addition, FIG. 3 shows the results of RT-PCR in the second test for the C74 line and the control, i.e., wild-type tomato without mutation. In the drawing, M represents molecular weight marker, P represents positive control, N represents negative control, and Mo represents Mock (i.e., inoculation of only the buffer), and lanes indicated "C74" below the lanes are the C74 line and lanes indicated "Cont" below the lanes are the control. The upper band shows the presence of the TSWV Infection rate was defined as a proportion of the sum of the number of plants showing disease symptoms (mosaic pattern, yellowing, necrosis, etc.) and the number of plants which are defined positive based on PCR, to the number of tested plants (number of samples), and the infection rate is shown in FIG. 4. In the drawing, the number in ( ) is the number of samples. As apparent from FIG. 4, the infection rate of the control was high, i.e., more than 0.5 to 0.8, but the infection rate of the RFL-edited line C74 was less than 0.4 at the highest. The test method used herein is a method with much higher infection pressure than a virus infection in nature by an insect vector. Therefore, the infection rate of less than 0.4 in the present test is suspected to be a level which causes no virus infection in nature.

Example 5

Example 5

<Confirmation of Mutation Pattern>

Method

From a T1 generation plant of C74 line, 0.1 g of true leaves were collected and total DNA was extracted from the leaves using MonoFas® Plant DNA Extraction Kit (manufactured and sold by GL Sciences® Inc.). Using the extracted DNA as a template, amplification products were obtained by PCR (Conditions: 2 minutes at 95° C.; 31 cycles of 10 seconds at 98° C., 20 seconds at 60° C., and 15 seconds at 68° C.; and 3 minutes at 72° C.) by using RLK detection primer 1 (5'-TTAACACGTCTGCGTAACCTC (SEQ ID NO: 4)) and primer 2 (5'-CCGGTGAAGGTAT-TGTAGTATCC (SEQ ID NO:5)) and a PCR enzyme KOD FX-Neo® (manufactured and sold by TAKARA BIO® INC.). The obtained amplification product was cloned into a cloning plasmid by using TA Cloning Kit TArgetClone® (TOYOBO® CO., LTD.) which is a TA cloning kit, and nucleotide sequence of the amplification product was determined by sequencing.

Results

Figures 5A, 5B:
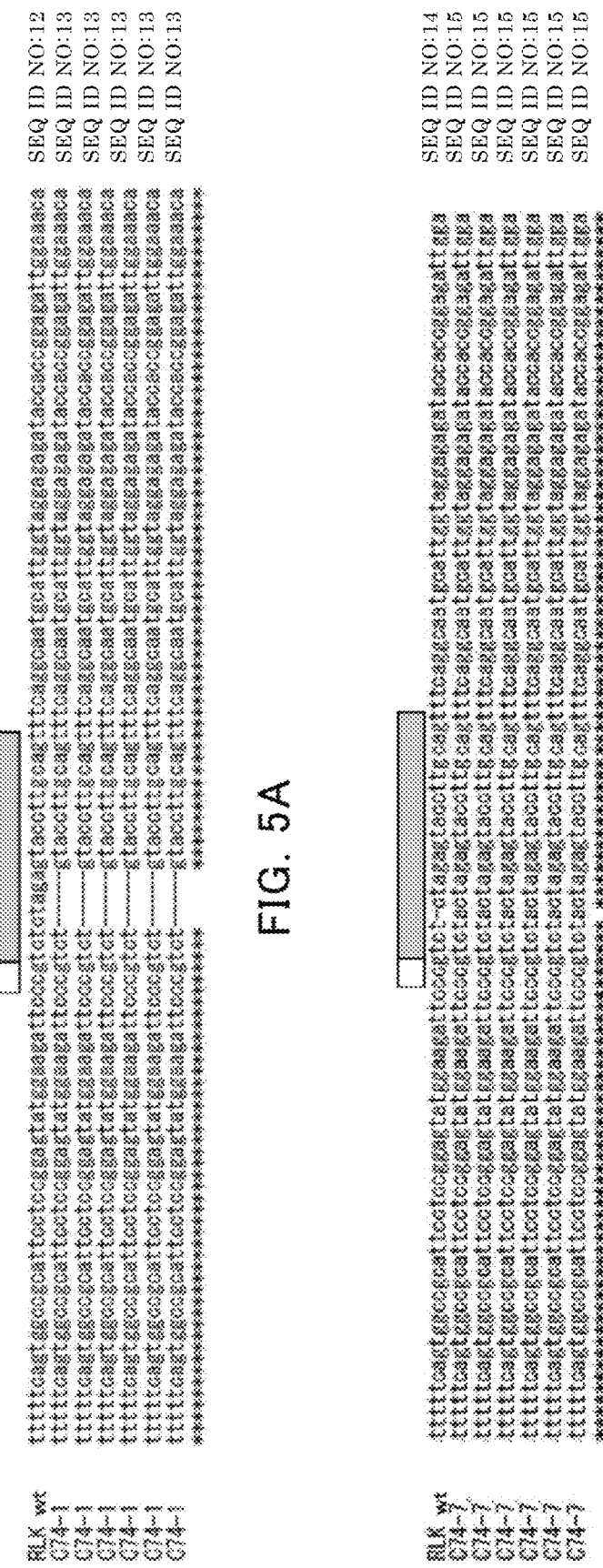
FIG. 5A shows the 5-nucleotide deletion in C74-1 line and FIG. 5B shows the 1-nucleotide insertion in C74-7 line.

The following mutation patterns were detected from the amplified region: first is 5-nucleotide deletion in the C74-1 line, and the other is a 1-nucleotide insertion in the C74-7 line. Confirmed nucleotide sequences are shown in FIG. 5(A) and FIG. 5(B), together with the nucleotide sequence of the wild-type. In FIG. 5, "RLK wt" represents the wild-type sequence, and the sequence of each clone is shown below the wild-type sequence; "CCG" shown in a white box is the PAM sequence; and the part shown in a grey box is the 20 nucleotides recognized by the guide RNA (however, the guide RNA actually recognizes the complementary strand (reverse strand)). Further, wild-type region, mutant region of the C74-1 line (mutant region R-A), and mutant region of the C74-7 line (mutant region R-B) are aligned in FIG. 6. In the drawing, underlined portion indicates the mutated part and "•" indicates the absence (loss) of a nucleotide.

This application is an application claiming priority based on Japanese Patent Application No. 2019-232766 filed on Dec. 24, 2019, and the contents described in the claims, description and drawings of the above-mentioned applications are incorporated herein by reference.

INDUSTRIAL APPLICABILITY

According to the present invention, there is provided a TSWV resistant solanaceous plant, a solanaceous plant cell, and a method for producing the solanaceous plant, and the solanaceous plant has inhibitory properties against: infection by TSWV, proliferation of the infected TSWV, and/or expression of TSWV infection symptoms. The present invention is capable of solving problems mainly in agricultural fields, such as decrease in solanaceous plant yield caused by TSWV infection.

Sequence Listing Free Text

SEQ ID NO:1: cDNA sequence of RLK gene (Solyc02g091840), 1st to 2818th nucleotides are exon 1, 790th to 809th nucleotides are target sequence;

SEQ ID NO:2: Exon 1 of RLK gene, and 790th to 809th nucleotides are target sequence;

SEQ ID NO:3: Target sequence in exon 1 of RLK gene;

SEQ ID NO:4: Primer 1 for detecting RLK gene;

SEQ ID NO:5: Primer 2 for detecting RLK gene;

SEQ ID NO:6: Primer 3 for detecting *Tospovirus;*

SEQ ID NO:7: Primer 4 for detecting *Tospovirus;*

SEQ ID NO:8: Mutated region R-A of RLK gene;

SEQ ID NO:9: Mutated region R-B of RLK gene;

SEQ ID NO:10: cDNA sequence of mutated RLK gene, and 790th to 804th nucleotides are mutated region R-A; and SEQ ID NO:11: cDNA sequence of mutated RLK gene, and 790th to 810th nucleotides are mutated region R-B.

[Sequence Listing]

---

The invention claimed is:

1. A solanaceous plant having a mutation in a receptor-like kinase RLK gene having a cDNA sequence comprising the nucleotide sequence as set forth in SEQ ID NO:1, wherein the solanaceous plant is obtained by introducing genomic gene mutation to the genome of the solanaceous plant by genome editing techniques, wherein the RLK gene is mutated to have a cDNA sequence comprising the nucleotide sequence as set forth in SEQ ID NO: 10 or SEQ ID NO: 11, wherein the mutation either inhibits expression of the mutated gene or makes a protein encoded by the mutated gene to be non-functional for tomato spotted wilt virus, and wherein the protein which is non-functional for the virus is either a protein which cannot be used by the virus during infection and replication, or a protein which reduces the infection and replication of the virus, as compared to a control solanaceous plant without the introduction of the mutation, and wherein the solanaceous plant has virus resistance against the tomato spotted wilt virus.

2. The solanaceous plant according to claim 1 which is a tomato.

3. A part of the solanaceous plant according to claim 1.

4. A processed material of the solanaceous plant according to claim 1 or a part thereof, wherein the processed material comprises at least one cell of the solanaceous plant having the mutation in the receptor-like kinase RLK gene.

5. A method for producing a tomato spotted wilt virus resistant solanaceous plant, the method comprising:

selecting the receptor-like kinase RLK gene having a cDNA sequence comprising the nucleotide sequence as set forth in SEQ ID NO:1;

introducing a mutation into the selected gene in a genome of a solanaceous plant by genome editing techniques, wherein the mutation is introduced so that the RLK gene has a cDNA sequence comprising the nucleotide sequence as set forth in SEQ ID NO: 10 or SEQ ID NO: 11, wherein the introduced mutation is either a mutation inhibiting an expression of the mutated gene or a mutation making a protein encoded by the mutated gene to be non-functional for tomato spotted wilt virus, and wherein the protein which is non-functional for the virus is either a protein which cannot be used by the virus during infection and replication, or a protein which reduces the infection and replication of the virus, as compared to a control solanaceous plant without the introduction of the mutation; and selecting the solanaceous plant showing lower infection rate for the tomato spotted wilt virus, as compared to control solanaceous plant without the introduction of the mutation, wherein the infection rate is based on the presence or absence of tomato spotted wilt virus symptoms judged by observation, and/or the presence or absence of a gene of the tomato spotted wilt virus detected by PCR, on day 20 or more post tomato spotted wilt virus inoculation.

6. A tomato spotted wilt virus resistant solanaceous plant obtained by the production method according to claim 5.

7. A method for producing a bred progeny of a tomato spotted wilt virus resistant solanaceous plant, the method comprising:

self-pollination or cross-pollination of either the tomato spotted wilt virus resistant solanaceous plant obtained by the production method according to claim 5 or a progeny of the tomato spotted wilt virus resistant solanaceous plant.

8. A tomato spotted wilt virus resistant solanaceous plant obtained by the production method of claim 7.

* * * * *

SEQUENCE LISTING

```
<160> NUMBER OF SEQ ID NOS: 15

<210> SEQ ID NO 1
<211> LENGTH: 3516
<212> TYPE: DNA
<213> ORGANISM: Solanum lycopersicum
<220> FEATURE:
<221> NAME/KEY: misc_feature
<222> LOCATION: (1)..(3516)
<223> OTHER INFORMATION: cDNA sequence of RLK gene
<220> FEATURE:
<221> NAME/KEY: misc_feature
<222> LOCATION: (1)..(2818)
<223> OTHER INFORMATION: Exon 1
<220> FEATURE:
<221> NAME/KEY: misc_feature
<222> LOCATION: (790)..(809)
<223> OTHER INFORMATION: Target sequence

<400> SEQUENCE: 1
gttacaaaaa agagttgggg cctcctctac ttgtacaatc tcacaattca aattttattt      60
ctttataata atcaatccct tcgtattata tttatttact caaaacaaaa gaatatacac     120
accaaacgga ttacccaccc tcaaaccaaa tcctcatttt tgcctttctc actctaactg     180
```

-continued

```
agtgaaactg caaaccaaac agtaggtggg cgttagatta acgaagcaaa aatgcgtctt      240
cttttttttc ttcttcttct tatgcatttt actgactttt ctgccggtaa acaaccacgc      300
ttaccggaat accaggcttt gcttgccctg aaaactgcca ttaccgatga cccgcagtta      360
actcttgcct catggaacat ctccaccagt cactgtacgt ggaatggtgt cacgtgcgac      420
acgcatcgtc acgtgacctc tcttgatatt tctgggttta atcttaccgg tactcttccg      480
ccggaagttg gaaatcttcg tttcttacaa aatttgtctg ttgctgttaa ccagtttact      540
ggacctgtac ctgttgaaat ctcctttatt ccaaatctga gttaccttaa tctttctaat      600
aacatattcg ggatggaatt cccttcgcag ttaacacgtc tgcgtaacct ccaagtcctt      660
gacctttaca acaacaatat gaccggtgaa cttcccgttg aggtgtatca gatgactaaa      720
cttcgacatc tacacctagg cgggaacttt ttcagtggcc gcattcctcc ggagtatgga      780
agattcccgt ctctagagta ccttgcagtt tcaggcaatg cattggtagg agagatacca      840
ccggagattg gaaacatcgc tacacttcag cagttgtatg taggatacta caataccttc      900
accggtggga ttccaccggc aatagggaac ttatcgcagc tccttcggtt tgatgctgct      960
aactgtggac tttcggggaa gattccaccg gagattggga agcttcagaa ccttgatacc     1020
ctcttcctgc aagtgaattc tctatctgga tctttaactc cggagatagg ttatctgaag     1080
agcttgaaat ctttggatct gtcgaataac atgttctctg gcgagatacc gccgacattt     1140
gcggagctta agaatatcac tcttgttaat cttttccgga ataagcttta tgggtcaata     1200
ccagagttca tagaggactt gccggaacta gaggtgttgc aactttggga aaataacttt     1260
actggaagca ttcctcaggg gttaggcaca aagagcaagc tcaaaactct tgatctcagt     1320
tccaataaat taacgggaaa tttacccccca aacatgtgct ccggtaacaa tctgcagaca     1380
attatcactc tagggaactt cttgtttggc ccaattcctg aatctttggg taggtgtgaa     1440
tcacttaatc gtattagaat gggagaaaat tatctgaatg ggtctattcc aaaagggctc     1500
ttaagcttgc cacatctgtc acaagttgaa cttcagaata atattctcac tggtacattt     1560
cctgatattt cttccaaatc taacagtctt ggccagatta tcctttcaaa taatcgctta     1620
actggacctt gccaccaag cattggaaac tttgctgtag cccaaaaatt gcttcttgat     1680
gggaacaaat tttcgggacg aattccagct gaaataggaa agcttcaaca gctatccaaa     1740
attgatttca gtcataacaa cttgtctgga cccattgctc cggagattag ccagtgcaag     1800
ttgctgactt atgttgatct cagcaggaac caactttcgg gtgagattcc tactgagatc     1860
acaggtatga gaatactcaa ctacttgaat ttatcgcgaa accacttagt tgggagtatt     1920 cctgcccta tttctagtat gcagagttta acttctgttg atttctcgta taacaacttt     1980
tctggtttag ttcctggaac cgggcaattt agttatttca attacacctc atttctaggc     2040
aatccagatc tttgcggacc ctatttgggc ccttgcaaag agggcgttgt tgatgggggtt     2100 agtcaacctc accaacgagg agccttaacg ccttcgatga agcttttact tgttataggt     2160
ttgcttgtct gttctattgt gtttgctgtt gctgcaatta taaaggcccg atctttaaag     2220
aaggcaagtg aagctcgtgc ctggaagcta actgcttttc agcgcctgga ttttacttgt     2280
gatgatattt tggatagctt gaaggaggat aacgttattg gaaaaggagg tgctggtatt     2340
gtctacaagg gggtaatgcc tagcgggggaa catgtagcgg ttaagaggtt gccagctatg     2400
agcaggggtt cctctcatga tcatgggttc aatgcagaga tacagactct tgggaggatc     2460
cgacacaggc acattgttag attattaggg tttttgctcga atcatgagac aaatcttttg     2520
gtttacgagt acatgcctaa tggaagtctt ggggaaatgc ttcatggcaa gaaaggcggt     2580
```

```
catttacatt gggataccag gtataagatt gccttggagt ctgctaaggg tctttgctat      2640
ctccatcacg attgctctcc tttgatcctc catcgtgatg tgaaatcaaa caacattctg      2700
ctggactcca gctttgaagc tcatgttgct gattttggac ttgctaagtt cttgcaagat      2760
tcagggacat cagaatgcat gtctgctatt gctggttctt atgggtacat tgctccagaa      2820
tatgcttaca cacttaaggt tgatgagaag agtgatgtat atagcttcgg tgtggtgcta      2880
ctagaactgg taagtggcaa aaaaccagtt ggagaatttg gtgatggtgt tgacatagtc      2940
caatgggtta ggaaaatgac tgatgggaaa aaggatggag ttctcaagat ccttgaccca      3000
agactctcaa cggttcccct taatgagtg atgcatgtct tctatgtcgc attgttgtgt      3060
gtcgaagagc aggctgtgga acgtcccacc atgcgagagg tagtgcaaat actaacggaa      3120
cttcccaagc caccaggtgc aaaatcagat gactcaaccg tcactgatca gtcgccccca      3180
tcagcctctg cattagagtc cccaacctca attcccgggg acacaaaaga ccatcatcaa      3240
ccaacacctc aatcacctcc acctgaccta ctcagtatct aatttgcaat gttcttgaag      3300
taggagtgtt ttatttagtt tgattctcta gttctattat gatcaattgt gctaagcttt      3360
attcctttgt tttaaaaaaa ttgggtcttt ctaggctcgg gggtttattc taactctaag      3420
atgggtttaa tgctcagaag ttttcctctt gtacagtaag attggtaggg ttttcaagtg      3480
tattattaaa tggaaaaaaa ttgcccttca tttgct                                3516
```

```
<210> SEQ ID NO 2
<211> LENGTH: 2818
<212> TYPE: DNA
<213> ORGANISM: Solanum lycopersicum
<220> FEATURE:
<221> NAME/KEY: misc_feature
<222> LOCATION: (1)..(2818)
<223> OTHER INFORMATION: Exon 1 of RLK gene
<220> FEATURE:
<221> NAME/KEY: misc_feature
<222> LOCATION: (790)..(809)
<223> OTHER INFORMATION: Target sequence

<400> SEQUENCE: 2
```

```
gttacaaaaa agagttgggg cctcctctac ttgtacaatc tcacaattca aattttattt        60
ctttataata atcaatccct tcgtattata tttatttact caaaacaaaa gaatatacac       120
accaaacgga ttacccaccc tcaaaccaaa tcctcatttt tgcctttctc actctaactg       180
agtgaaactg caaaccaaac agtaggtggg cgttagatta acgaagcaaa aatgcgtctt       240
cttttttttc ttcttcttct tatgcatttt actgactttt ctgccggtaa acaaccacgc       300
ttaccggaat accaggcttt gcttgccctg aaaactgcca ttaccgatga cccgcagtta       360
actcttgcct catggaacat ctccaccagt cactgtacgt ggaatggtgt cacgtgcgac       420
acgcatcgtc acgtgacctc tcttgatatt tctgggttta atcttaccgg tactcttccg       480
ccggaagttg gaaatcttcg tttcttacaa aatttgtctg ttgctgttaa ccagtttact       540
ggacctgtac ctgttgaaat ctcctttatt ccaaatctga gttaccttaa tctttctaat       600
aacatattcg ggatggaatt cccttcgcag ttaacacgtc tgcgtaacct ccaagtcctt       660
gacctttaca acaacaatat gaccggtgaa cttcccgttg aggtgtatca gatgactaaa       720
cttcgacatc tacacctagg cgggaacttt ttcagtggcc gcattcctcc ggagtatgga       780
agattcccgt ctctagagta ccttgcagtt tcaggcaatg cattggtagg agagatacca       840
ccggagattg gaaacatcgc tacacttcag cagttgtatg taggatacta caatacccttc       900
```

-continued

```
accggtggga ttccaccggc aatagggaac ttatcgcagc tccttcggtt tgatgctgct      960
aactgtggac tttcggggaa gattccaccg gagattggga agcttcagaa ccttgatacc     1020
ctcttcctgc aagtgaattc tctatctgga tctttaactc cggagatagg ttatctgaag     1080
agcttgaaat ctttggatct gtcgaataac atgttctctg gcgagatacc gccgacattt     1140
gcggagctta agaatatcac tcttgttaat cttttccgga ataagcttta tgggtcaata     1200
ccagagttca tagaggactt gccggaacta gaggtgttgc aactttggga aaataacttt     1260
actggaagca ttcctcaggg gttaggcaca aagagcaagc tcaaaactct tgatctcagt     1320
tccaataaat taacgggaaa tttaccccca aacatgtgct ccggtaacaa tctgcagaca     1380
attatcactc tagggaactt cttgtttggc ccaattcctg aatctttggg taggtgtgaa     1440
tcacttaatc gtattagaat gggagaaaat tatctgaatg ggtctattcc aaaagggctc     1500
ttaagcttgc cacatctgtc acaagttgaa cttcagaata atattctcac tggtacattt     1560
cctgatattt cttccaaatc taacagtctt ggccagatta tcctttcaaa taatcgctta     1620
actggacctt tgccaccaag cattggaaac tttgctgtag cccaaaaatt gcttcttgat     1680
gggaacaaat tttcgggacg aattccagct gaaataggaa agcttcaaca gctatccaaa     1740
attgatttca gtcataacaa cttgtctgga cccattgctc cggagattag ccagtgcaag     1800
ttgctgactt atgttgatct cagcaggaac caactttcgg gtgagattcc tactgagatc     1860
acaggtatga gaatactcaa ctacttgaat ttatcgcgaa accacttagt tgggagtatt     1920
cctgccccta tttctagtat gcagagttta acttctgttg atttctcgta taacaacttt     1980
tctggtttag ttcctggaac cgggcaattt agttatttca attacacctc atttctaggc     2040
aatccagatc tttgcggacc ctatttgggc ccttgcaaag agggcgttgt tgatgggggtt     2100 agtcaacctc accaacgagg agccttaacg ccttcgatga agctttact tgttataggt     2160 ttgcttgtct gttctattgt gtttgctgtt gctgcaatta taaaggcccg atctttaaag     2220
aaggcaagtg aagctcgtgc ctggaagcta actgctttc agcgcctgga ttttacttgt     2280
gatgatattt tggatagctt gaaggaggat aacgttattg gaaaaggagg tgctggtatt     2340
gtctacaagg gggtaatgcc tagcggggaa catgtagcgg ttaagaggtt gccagctatg     2400
agcaggggtt cctctcatga tcatgggttc aatgcagaga tacagactct tgggaggatc     2460
cgacacaggc acattgttag attattaggg ttttgctcga atcatgagac aaatctttg     2520 gtttacgagt acatgcctaa tggaagtctt ggggaaatgc ttcatggcaa gaaaggcggt     2580
catttacatt gggataccag gtataagatt gccttggagt ctgctaaggg tctttgctat     2640
ctccatcacg attgctctcc tttgatcctc catcgtgatg tgaaatcaaa caacattctg     2700
ctggactcca gctttgaagc tcatgttgct gattttggac ttgctaagtt cttgcaagat     2760
tcagggacat cagaatgcat gtctgctatt gctggttctt atgggtacat tgctccag      2818
```

```
<210> SEQ ID NO 3
<211> LENGTH: 20
<212> TYPE: DNA
<213> ORGANISM: Solanum lycopersicum
<220> FEATURE:
<221> NAME/KEY: misc_feature
<222> LOCATION: (1)..(20)
<223> OTHER INFORMATION: Target sequence in exon 1 of RLK gene

<400> SEQUENCE: 3
tctctagagt accttgcagt                                                    20
```

-continued

```
<210> SEQ ID NO 4
<211> LENGTH: 21
<212> TYPE: DNA
<213> ORGANISM: Artificial Sequence
<220> FEATURE:
<223> OTHER INFORMATION: Primer 1 for RLK

<400> SEQUENCE: 4
ttaacacgtc tgcgtaacct c                                            21

<210> SEQ ID NO 5
<211> LENGTH: 23
<212> TYPE: DNA
<213> ORGANISM: Artificial Sequence
<220> FEATURE:
<223> OTHER INFORMATION: Primer 2 for RLK

<400> SEQUENCE: 5
ccggtgaagg tattgtagta tcc                                          23

<210> SEQ ID NO 6
<211> LENGTH: 21
<212> TYPE: DNA
<213> ORGANISM: Artificial Sequence
<220> FEATURE:
<223> OTHER INFORMATION: Primer 3 for Tospo virus species

<400> SEQUENCE: 6
ctgtartgkt ccatwgcarc a                                            21

<210> SEQ ID NO 7
<211> LENGTH: 24
<212> TYPE: DNA
<213> ORGANISM: Artificial Sequence
<220> FEATURE:
<223> OTHER INFORMATION: Primer 4 for Tospo virus species

<400> SEQUENCE: 7
gayatgacyt tcmgaagrct tgat                                         24

<210> SEQ ID NO 8
<211> LENGTH: 15
<212> TYPE: DNA
<213> ORGANISM: Solanum lycopersicum
<220> FEATURE:
<221> NAME/KEY: misc_feature
<222> LOCATION: (1)..(15)
<223> OTHER INFORMATION: Mutated region R-A of RLK gene

<400> SEQUENCE: 8
tctgtacctt gcagt                                                   15

<210> SEQ ID NO 9
<211> LENGTH: 21
<212> TYPE: DNA
<213> ORGANISM: Solanum lycopersicum
<220> FEATURE:
<221> NAME/KEY: misc_feature
<222> LOCATION: (1)..(21)
<223> OTHER INFORMATION: Mutated region R-B of RLK gene

<400> SEQUENCE: 9
tctactagag taccttgcag t                                            21

<210> SEQ ID NO 10
<211> LENGTH: 3511
<212> TYPE: DNA
```

-continued

```
<213> ORGANISM: Solanum lycopersicum
<220> FEATURE:
<221> NAME/KEY: misc_feature
<222> LOCATION: (1)..(3511)
<223> OTHER INFORMATION: DNA sequence of mutated RLK gene
<220> FEATURE:
<221> NAME/KEY: misc_difference
<222> LOCATION: (790)..(804)
<223> OTHER INFORMATION: Mutated region R-A

<400> SEQUENCE: 10
gttacaaaaa agagttgggg cctcctctac ttgtacaatc tcacaattca aattttattt        60
ctttataata atcaatccct tcgtattata tttatttact caaaacaaaa gaatatacac       120
accaaacgga ttacccaccc tcaaaccaaa tcctcatttt tgcctttctc actctaactg       180
agtgaaactg caaaccaaac agtaggtggg cgttagatta acgaagcaaa aatgcgtctt       240
cttttttttc ttcttcttct tatgcatttt actgactttt ctgccggtaa acaaccacgc       300
ttaccggaat accaggcttt gcttgccctg aaaactgcca ttaccgatga cccgcagtta       360
actcttgcct catggaacat ctccaccagt cactgtacgt ggaatggtgt cacgtgcgac       420
acgcatcgtc acgtgacctc tcttgatatt tctgggttta atcttaccgg tactcttccg       480
ccggaagttg gaaatcttcg tttcttacaa aatttgtctg ttgctgttaa ccagtttact       540
ggacctgtac ctgttgaaat ctcctttatt ccaaatctga gttaccttaa tctttctaat       600
aacatattcg ggatggaatt cccttcgcag ttaacacgtc tgcgtaacct ccaagtcctt       660
gacctttaca acaacaatat gaccggtgaa cttcccgttg aggtgtatca gatgactaaa       720
cttcgacatc tacacctagg cgggaacttt ttcagtggcc gcattcctcc ggagtatgga       780
agattcccgt ctgtaccttg cagtttcagg caatgcattg gtaggagaga taccaccgga       840
gattggaaac atcgctacac ttcagcagtt gtatgtagga tactacaata ccttcaccgg       900
tgggattcca ccggcaatag ggaacttatc gcagctcctt cggtttgatg ctgctaactg       960
tggactttcg gggaagattc caccggagat tgggaagctt cagaaccttg atacctcttt      1020
cctgcaagtg aattctctat ctggatcttt aactccggag ataggttatc tgaagagctt      1080
gaaatctttg gatctgtcga ataacatgtt ctctggcgag ataccgccga catttgcgga      1140
gcttaagaat atcactcttg ttaatctttt ccggaataag ctttatgggt caataccaga      1200
gttcatagag gacttgccgg aactagaggt gttgcaactt tgggaaaata actttactgg      1260
aagcattcct caggggttag gcacaaagag caagctcaaa actcttgatc tcagttccaa      1320
taaattaacg ggaaatttac ccccaaacat gtgctccggt aacaatctgc agacaattat      1380
cactctaggg aacttcttgt ttggcccaat tcctgaatct ttgggtaggt gtgaatcact      1440
taatcgtatt agaatgggag aaaattatct gaatgggtct attccaaaag ggctcttaag      1500
cttgccacat ctgtcacaag ttgaacttca gaataatatt ctcactggta catttcctga      1560
tatttcttcc aaatctaaca gtcttggcca gattatcctt tcaaataatc gcttaactgg      1620
acctttgcca ccaagcattg gaaactttgc tgtagcccaa aaattgcttc ttgatgggaa      1680
caaattttcg ggacgaattc cagctgaaat aggaaagctt caacagctat ccaaaattga      1740
tttcagtcat aacaacttgt ctggacccat tgctccggag attagccagt gcaagttgct      1800
gacttatgtt gatctcagca ggaaccaact ttcgggtgag attcctactg agatcacagg      1860
tatgagaata ctcaactact tgaatttatc gcgaaaccac ttagttggga gtattcctgc      1920
ccctatttct agtatgcaga gtttaacttc tgttgatttc tcgtataaca acttttctgg      1980
tttagttcct ggaaccgggc aatttagtta tttcaattac acctcatttc taggcaatcc      2040
```

-continued

```
agatctttgc ggaccctatt tgggcccttg caaagagggc gttgttgatg gggttagtca      2100
acctcaccaa cgaggagcct taacgccttc gatgaagctt ttacttgtta taggtttgct      2160
tgtctgttct attgtgtttg ctgttgctgc aattataaag gcccgatctt taaagaaggc      2220
aagtgaagct cgtgcctgga agctaactgc ttttcagcgc ctggatttta cttgtgatga      2280
tattttggat agcttgaagg aggataacgt tattggaaaa ggaggtgctg gtattgtcta      2340 caaggggggta atgcctagcg gggaacatgt agcggttaag aggttgccag ctatgagcag      2400
gggttcctct catgatcatg ggttcaatgc agagatacag actcttggga ggatccgaca      2460
caggcacatt gttagattat tagggttttg ctcgaatcat gagacaaatc ttttggttta      2520
cgagtacatg cctaatggaa gtcttgggga aatgcttcat ggcaagaaag gcggtcattt      2580
acattgggat accaggtata agattgcctt ggagtctgct aagggtcttt gctatctcca      2640
tcacgattgc tctcctttga tcctccatcg tgatgtgaaa tcaaacaaca ttctgctgga      2700
ctccagcttt gaagctcatg ttgctgattt tggacttgct aagttcttgc aagattcagg      2760
gacatcagaa tgcatgtctg ctattgctgg ttcttatggg tacattgctc cagaatatgc      2820
ttacacactt aaggttgatg agaagagtga tgtatatagc ttcggtgtgg tgctactaga      2880
actggtaagt ggcaaaaaac cagttggaga atttggtgat ggtgttgaca tagtccaatg      2940
ggttaggaaa atgactgatg ggaaaaagga tggagttctc aagatccttg acccaagact      3000
ctcaacggtt ccccttaatg aggtgatgca tgtcttctat gtcgcattgt tgtgtgtcga      3060
agagcaggct gtggaacgtc ccaccatgcg agaggtagtg caaatactaa cggaacttcc      3120
caagccacca ggtgcaaaat cagatgactc aaccgtcact gatcagtcgc ccccatcagc      3180
ctctgcatta gagtccccaa cctcaattcc cggggacaca aaagaccatc atcaaccaac      3240
acctcaatca cctccacctg acctactcag tatctaattt gcaatgttct tgaagtagga      3300
gtgttttatt tagtttgatt ctctagttct attatgatca attgtgctaa gctttattcc      3360 tttgtttttaa aaaaattggg tctttctagg ctcggggggtt tattctaact ctaagatggg      3420
tttaatgctc agaagttttc ctcttgtaca gtaagattgg tagggttttc aagtgtatta      3480
ttaaatggaa aaaaattgcc cttcatttgc t      3511
```

<210> SEQ ID NO 11
<211> LENGTH: 3517
<212> TYPE: DNA
<213> ORGANISM: Solanum lycopersicum
<220> FEATURE:
<221> NAME/KEY: misc_feature
<222> LOCATION: (1)..(3517)
<223> OTHER INFORMATION: cDNA sequence of mutated RLK gene
<220> FEATURE:
<221> NAME/KEY: misc_difference
<222> LOCATION: (790)..(810)
<223> OTHER INFORMATION: Mutated region R-B

<400> SEQUENCE: 11

```
gttacaaaaa agagttgggg cctcctctac ttgtacaatc tcacaattca aatttttattt       60 ctttataata atcaatccct tcgtattata tttatttact caaaacaaaa gaatatacac      120
accaaacgga ttacccaccc tcaaaccaaa tcctcatttt tgcctttctc actctaactg      180
agtgaaactg caaaccaaac agtaggtggg cgttagatta acgaagcaaa aatgcgtctt      240
cttttttttc ttcttcttct tatgcatttt actgactttt ctgccggtaa acaaccacgc      300
ttaccggaat accaggcttt gcttgccctg aaaactgcca ttaccgatga cccgcagtta      360
```

-continued

```
actcttgcct catggaacat ctccaccagt cactgtacgt ggaatggtgt cacgtgcgac    420
acgcatcgtc acgtgacctc tcttgatatt tctgggttta atcttaccgg tactcttccg    480
ccggaagttg gaaatcttcg tttcttacaa aatttgtctg ttgctgttaa ccagtttact    540
ggacctgtac ctgttgaaat ctcctttatt ccaaatctga gttaccttaa tctttctaat    600
aacatattcg ggatggaatt cccttcgcag ttaacacgtc tgcgtaacct ccaagtcctt    660
gacctttaca acaacaatat gaccggtgaa cttcccgttg aggtgtatca gatgactaaa    720
cttcgacatc tacacctagg cgggaacttt ttcagtggcc gcattcctcc ggagtatgga    780
agattcccgt ctactagagt accttgcagt ttcaggcaat gcattggtag gagagatacc    840
accggagatt ggaaacatcg ctacacttca gcagttgtat gtaggatact acaatacctt    900
caccggtggg attccaccgg caatagggaa cttatcgcag ctccttcggt ttgatgctgc    960
taactgtgga ctttcgggga agattccacc ggagattggg aagcttcaga accttgatac   1020
cctcttcctg caagtgaatt ctctatctgg atctttaact ccggagatag gttatctgaa   1080
gagcttgaaa tctttggatc tgtcgaataa catgttctct ggcgagatac cgccgacatt   1140
tgcggagctt aagaatatca ctcttgttaa tcttttccgg aataagcttt atgggtcaat   1200
accagagttc atagaggact tgccggaact agaggtgttg caactttggg aaaataactt   1260
tactggaagc attcctcagg ggttaggcac aaagagcaag ctcaaaactc ttgatctcag   1320
ttccaataaa ttaacgggaa atttacccc aaacatgtgc tccggtaaca atctgcagac   1380
aattatcact ctagggaact tcttgtttgg cccaattcct gaatctttgg gtaggtgtga   1440
atcacttaat cgtattagaa tgggagaaaa ttatctgaat gggtctattc caaaagggct   1500
cttaagcttg ccacatctgt cacaagttga acttcagaat aatattctca ctggtacatt   1560
tcctgatatt tcttccaaat ctaacagtct tggccagatt atcctttcaa ataatcgctt   1620
aactggacct ttgccaccaa gcattggaaa ctttgctgta gcccaaaaat tgcttcttga   1680
tgggaacaaa ttttcgggac gaattccagc tgaaatagga aagcttcaac agctatccaa   1740
aattgatttc agtcataaca acttgtctgg acccattgct ccggagatta gccagtgcaa   1800
gttgctgact tatgttgatc tcagcaggaa ccaactttcg ggtgagattc ctactgagat   1860
cacaggtatg agaatactca actacttgaa tttatcgcga aaccacttag ttgggagtat   1920
tcctgcccct atttctagta tgcagagttt aacttctgtt gatttctcgt ataacaactt   1980 ttctggtttta gttcctggaa ccgggcaatt tagttatttc aattacacct catttctagg   2040
caatccagat ctttgcggac cctatttggg ccccttgcaaa gagggcgttg ttgatggggt   2100
tagtcaacct caccaacgag gagccttaac gccttcgatg aagcttttac ttgttatagg   2160
tttgcttgtc tgttctattg tgtttgctgt tgctgcaatt ataaaggccc gatctttaaa   2220
gaaggcaagt gaagctcgtg cctggaagct aactgctttt cagcgcctgg attttacttg   2280
tgatgatatt ttggatagct tgaaggagga taacgttatt ggaaaaggag gtgctggtat   2340
tgtctacaag ggggtaatgc ctagcgggga acatgtagcg gttaagaggt tgccagctat   2400
gagcaggggt tcctctcatg atcatgggtt caatgcagag atacagactc ttgggaggat   2460
ccgacacagg cacattgtta gattattagg gttttgctcg aatcatgaga caaatctttt   2520
ggtttacgag tacatgccta atggaagtct tggggaaatg cttcatggca agaaaggcgg   2580
tcatttacat tgggatacca ggtataagat tgccttggag tctgctaagg gtctttgcta   2640
tctccatcac gattgctctc ctttgatcct ccatcgtgat gtgaaatcaa acaacattct   2700
gctggactcc agctttgaag ctcatgttgc tgattttgga cttgctaagt cttgcaaga   2760
```

```
ttcagggaca tcagaatgca tgtctgctat tgctggttct tatgggtaca ttgctccaga    2820
atatgcttac acacttaagg ttgatgagaa gagtgatgta tatagcttcg gtgtggtgct    2880
actagaactg gtaagtggca aaaaaccagt tggagaattt ggtgatggtg ttgacatagt    2940
ccaatgggtt aggaaaatga ctgatgggaa aaaggatgga gttctcaaga tccttgaccc    3000
aagactctca acggttcccc ttaatgaggt gatgcatgtc ttctatgtcg cattgttgtg    3060
tgtcgaagag caggctgtgg aacgtcccac catgcgagag gtagtgcaaa tactaacgga    3120
acttcccaag ccaccaggtg caaaatcaga tgactcaacc gtcactgatc agtcgcccccc    3180 atcagcctct gcattagagt ccccaacctc aattcccggg gacacaaaag accatcatca    3240
accaacacct caatcacctc cacctgacct actcagtatc taatttgcaa tgttcttgaa    3300
gtaggagtgt tttatttagt ttgattctct agttctatta tgatcaattg tgctaagctt    3360
tattcctttg ttttaaaaaa attgggtctt tctaggctcg ggggtttatt ctaactctaa    3420
gatgggttta atgctcagaa gttttcctct tgtacagtaa gattggtagg gttttcaagt    3480
gtattattaa atggaaaaaa attgcccttc atttgct                             3517
```

```
<210> SEQ ID NO 12
<211> LENGTH: 109
<212> TYPE: DNA
<213> ORGANISM: Artificial Sequence
<220> FEATURE:
<223> OTHER INFORMATION: RLK wt of FIG. 5(A)

<400> SEQUENCE: 12
tttttcagtg gccgcattcc tccggagtat ggaagattcc cgtctctaga gtaccttgca     60
gtttcaggca atgcattggt aggagagata ccaccggaga ttggaaaca              109
```

```
<210> SEQ ID NO 13
<211> LENGTH: 104
<212> TYPE: DNA
<213> ORGANISM: Artificial Sequence
<220> FEATURE:
<223> OTHER INFORMATION: C74-1 of FIG. 5(A)

<400> SEQUENCE: 13
tttttcagtg gccgcattcc tccggagtat ggaagattcc cgtctgtacc ttgcagtttc     60
aggcaatgca ttggtaggag agataccacc ggagattgga aaca                   104
```

```
<210> SEQ ID NO 14
<211> LENGTH: 105
<212> TYPE: DNA
<213> ORGANISM: Artificial Sequence
<220> FEATURE:
<223> OTHER INFORMATION: RLK wt of FIG. 5(B)

<400> SEQUENCE: 14
tttttcagtg gccgcattcc tccggagtat ggaagattcc cgtctctaga gtaccttgca     60
gtttcaggca atgcattggt aggagagata ccaccggaga ttgga                  105
```

```
<210> SEQ ID NO 15
<211> LENGTH: 110
<212> TYPE: DNA
<213> ORGANISM: Artificial Sequence
<220> FEATURE:
<223> OTHER INFORMATION: C74-7 of FIG. 5(B)

<400> SEQUENCE: 15
```

-continued

| | | | | | |
|---|---|---|---|---|---|
| tttttcagtg | gccgcattcc | tccggagtat | ggaagattcc | cgtctactag | agtaccttgc | 60 |
| agtttcaggc | aatgcattgg | taggagagat | accaccggag | attggaaaca | | 110 |